US009642917B2

United States Patent
Wu et al.

(10) Patent No.: US 9,642,917 B2
(45) Date of Patent: *May 9, 2017

(54) USE OF G-CSF DIMER IN PREPARATION OF MEDICAMENT FOR TREATMENT OF NEURODEGENERATIVE DISEASES

(75) Inventors: Dong-Dong Wu, Shanghai (CN); Zhihua Huang, Shanghai (CN); Yuliang Huang, Shanghai (CN); Xiaoqiang Yan, Shanghai (CN)

(73) Assignee: GENERON (SHANGHAI) CORPORATION, LTD., Shanghai (CN)

(*) Notice: Subject to any disclaimer, the term of this patent is extended or adjusted under 35 U.S.C. 154(b) by 0 days.

This patent is subject to a terminal disclaimer.

(21) Appl. No.: 14/233,739

(22) PCT Filed: Jul. 24, 2012

(86) PCT No.: PCT/CN2012/079106
§ 371 (c)(1),
(2), (4) Date: May 5, 2014

(87) PCT Pub. No.: WO2013/013613
PCT Pub. Date: Jan. 31, 2013

(65) Prior Publication Data
US 2014/0248234 A1    Sep. 4, 2014

(30) Foreign Application Priority Data
Jul. 25, 2011    (CN) .......................... 2011 1 0209712

(51) Int. Cl.
| C07K 16/00 | (2006.01) |
| C07K 14/535 | (2006.01) |
| C12N 15/09 | (2006.01) |
| C12N 15/24 | (2006.01) |
| A61P 25/00 | (2006.01) |
| A61K 47/48 | (2006.01) |
| A61K 38/19 | (2006.01) |

(52) U.S. Cl.
CPC ........ *A61K 47/48269* (2013.01); *A61K 38/19* (2013.01)

(58) Field of Classification Search
None
See application file for complete search history.

(56) References Cited

U.S. PATENT DOCUMENTS

| 5,665,863 A | 9/1997 | Yeh |
| 6,254,870 B1 | 7/2001 | Staten et al. |
| 6,331,613 B1 | 12/2001 | Dumoutier et al. |
| 6,359,117 B1 | 3/2002 | Dumoutier et al. |
| 6,551,799 B2 | 4/2003 | Gurney et al. |
| 6,797,493 B2 | 9/2004 | Sun et al. |
| 6,900,292 B2 | 5/2005 | Sun et al. |
| 7,169,905 B2 | 1/2007 | Feige |
| 7,226,759 B2 | 6/2007 | Sun et al. |
| 7,232,668 B2 | 6/2007 | Sun et al. |
| 7,307,161 B1 | 12/2007 | Jacobs et al. |
| 7,459,533 B2 | 12/2008 | Jacobs et al. |
| 7,585,646 B2 | 9/2009 | Jacobs et al. |
| 7,625,564 B2 | 12/2009 | Wang et al. |
| 7,666,402 B2 | 2/2010 | Huang et al. |
| 7,696,158 B2 | 4/2010 | Huang et al. |
| 7,718,604 B2 | 5/2010 | Huang et al. |
| 7,723,302 B2 | 5/2010 | Wu et al. |
| 7,785,601 B2 | 8/2010 | Schaebitz et al. |
| 7,972,833 B2 | 7/2011 | Dumoutier et al. |
| 8,048,984 B2 | 11/2011 | Jacobs et al. |
| 8,557,546 B2 | 10/2013 | Yan et al. |
| 9,273,108 B2 * | 3/2016 | Yan ...................... C07K 14/535 |
| 2002/0142964 A1 | 10/2002 | Nissen et al. |
| 2003/0082679 A1 | 5/2003 | Sun et al. |
| 2004/0259209 A1 | 12/2004 | Sun et al. |
| 2006/0153799 A1 | 7/2006 | Zhao et al. |
| 2008/0300188 A1 | 12/2008 | Yang et al. |
| 2009/0202475 A1 | 8/2009 | Abbas et al. |
| 2009/0203601 A1 | 8/2009 | Soni et al. |
| 2011/0262385 A1 | 10/2011 | Huang et al. |

(Continued)

FOREIGN PATENT DOCUMENTS

| CN | 1410450 A | 4/2003 |
| CN | 102260343 A | 11/2011 |

(Continued)

OTHER PUBLICATIONS

Donahue et al., 2008, J. Neuropathol. Exp. Neurol., 67(4):261-70.*
Persidsky et al., J. Neuroimmune Pharmacol., 2006, 1:223-36.*
Chen et al., J. Alzheimer's disease, 2010, 20:S127-S141.*
Carvey et al., J. Neurochemistry, 2009, 111(2):291-314.*
Extended European Search Report mailed on Feb. 13, 2015, for European Patent Application No. 12 817 542.9, filed Jul. 24, 2012, five pages.

(Continued)

*Primary Examiner* — Olga N Chernyshev
(74) *Attorney, Agent, or Firm* — Morrison & Foerster LLP

(57) ABSTRACT

The invention discloses the use of the G-CSF dimer in the preparation of a medicament for the treatment of neurodegenerative diseases. Use of the G-CSF dimer of the present invention can significantly increase the number of dopaminergic neuron in the substantia nigra in PD model animals and enhance the function of dopaminergic neurons. In addition, the G-CSF dimer can significantly reduce apoptosis of neuron in hippocampus and improve learning and memory ability of AD model rats. Serum half-life of the G-CSF dimer of the invention is prolonged and the loss of neurons is effectively prevented, providing a better therapeutic effect in treatment of neurodegenerative disease.

20 Claims, 3 Drawing Sheets

(56) References Cited

U.S. PATENT DOCUMENTS

| | | |
|---|---|---|
| 2011/0280828 A1 | 11/2011 | Abbas et al. |
| 2012/0231065 A1 | 9/2012 | Schaebitz et al. |
| 2013/0165637 A1 | 6/2013 | Yan et al. |
| 2014/0004076 A1 | 1/2014 | Yan et al. |
| 2015/0147290 A1 | 5/2015 | Yan et al. |

FOREIGN PATENT DOCUMENTS

| | | |
|---|---|---|
| CN | 102380090 A | 3/2012 |
| CN | 102906120 A | 1/2013 |
| EP | 2 612 676 A1 | 7/2013 |
| JP | H07-503844 A | 4/1995 |
| JP | 2003-508023 A | 1/2001 |
| JP | 2004-131507 A | 4/2004 |
| JP | 2010-531134 A | 9/2010 |
| LT | 2 010 012 A | 8/2011 |
| LT | 2 010 013 A | 8/2011 |
| WO | WO-93/15211 A1 | 8/1993 |
| WO | WO-01/03737 A1 | 1/2001 |
| WO | WO-02/29098 A2 | 4/2002 |
| WO | WO-02/36626 A1 | 5/2002 |
| WO | WO-03/076567 A2 | 9/2003 |
| WO | WO-03/076567 A3 | 9/2003 |
| WO | WO-2008/147143 A2 | 12/2008 |
| WO | WO-2008/147143 A3 | 12/2008 |
| WO | WO-2009/019441 A2 | 2/2009 |
| WO | WO-2009/019441 A3 | 2/2009 |
| WO | WO-2010/011735 A2 | 1/2010 |
| WO | WO-2010/011735 A3 | 1/2010 |
| WO | WO-2011/087986 A1 | 7/2011 |
| WO | WO-2011/147319 A1 | 12/2011 |
| WO | WO-2012/028093 A1 | 3/2012 |

OTHER PUBLICATIONS

Fidler, K. et al (Mar. 2011). "The Characterization and Potential Use of G-CSF Dimers and their Pegylated Conjugates," *Acta Chim. Slov.* 58(1):1-8.

Hu, Z.T. et al. (2010). "F-627, a G-CSF Dimer, Stimulated a More Rapid Neutrophil Recovery in Cyclophosphamide-Treated Monkeys Compared to Monomer Rhg-CSFs," *Blood* 116:634 (Abstract 1485).

Cox, G.N. et al. (May 2004). "Enhanced Circulating Half-Life and Hematopoietic Properties of a Human Granulocyte Colony-Stimulating Factor/Immunoglobulin Fusion Protein," *Exp. Hematol.* 32(5):441-449.

European Office Action mailed on Mar. 19, 2014 for European Patent Application No. 12 817 542.9, filed on Jul. 24, 2012, three pages.

Guo, S. et al. (Nov. 2003). "Construction and Expression, Biological Activities and Protein Characteristics Analysis of Human Recombinant Bimolecular G-CSF," *Letters in Biotechnology* 14(6):489-493 (English Translation of Abstract Only).

International Search Report mailed on Nov. 1, 2012, for PCT Patent Application No. PCT/CN2012/079106, filed on Jul. 24, 2012, 6 pages.

Nutt, J.G. et al. (Jan. 14, 2003). "Randomized, Double-Blind Trial of Glial Cell Line-Derived Neurotrophic Factor (GDNF) in PD," *Neurology* 60(1)69-73.

Schabitz, W.R. et al. (Mar. 2003; e-pub. Feb. 13, 2003). "Neuroprotective Effect of Granulocyte Colony-Stimulating Factor After Focal Cerebral Ischemia," *Stroke* 34(3):745-751.

Schneider, A. et al. (Aug. 2005; e-pub. Jul. 7, 2005). "The Hematopoietic Factor G-CSF is a Neuronal Ligand That Counteracts Programmed Cell Death and Drives Neurogenesis," *J. Clin. Invest.* 115(8):2083-2098.

Shyu, W.C. et al. (Mar. 28, 2006; e-pub. Mar. 3, 2006). "Granulocyte Colony-Stimulating Factor for Acute Ischemic Stroke: A Randomized Controlled Trial," *CMAJ* 174(7):927-933.

Song, S. et al. (Jan. 7, 2011; e-pub. Oct. 14, 2010). "Granulocyte-Colony Stimulating Factor (G-CSF) Enhances Recovery in Mouse Model of Parkinson's Disease," *Neuroscience Letters* 487(2):153-157.

Tamada, T. et al. (Feb. 28, 2006; e-pub. Feb. 21, 2006). "Homodimeric Cross-Over Structure of the Human Granulocyte Colony-Stimulating Factor (GCSF) Receptor Signaling Complex," *PNAS* 103(9):3135-3140.

Tsai, K.J. et al. (Jun. 11, 2007; e-pub. May 21, 2007). "G-CSF Rescues the Memory Impairment of Animal Models of Alzheimer's Disease," *J. Exp. Med.* 204(6):1273-1280.

Written Opinion of the International Searching Authority mailed on Nov. 1, 2012, for PCT Patent Application No. PCT/CN2012/079106, filed on Jul. 24, 2012, 10 pages.

Aritomi, M. et al. (1999). "Atomic structure of the GCSF-receptor complex showing a new cytokine-receptor recognition scheme," *Nature* 401(6754):713-717.

Bowie, J.U. et al. (Mar. 16, 1990). "Deciphering the Message in Protein Sequences: Tolerances to Amino Acid Substitutions," *Science* 247(4948):1306-1310.

Burgess, W.H. et al. (Nov. 1, 1990). "Possible Dissociation of the Heparin-Binding and Mitogenic Activities of Heparin-Binding (Acidic Fibroblast) Growth Factor-1 from Its Receptor-Binding Activities by Site-Directed Mutagenesis of a Single Lysine Residue," *J. Cell Biology* 111:2129-2138.

Extended European Search Report mailed on Oct. 16, 2013, for European Patent Application No. 11 786 091.6, filed on May 25, 2011, 12 pages.

Extended European Search Report mailed on Jan. 7, 2014, for European Patent Application No. 11 821119.2, filed on May 25, 2011, 26 pages.

European Office Action mailed on Sep. 4, 2014, for European Patent Application No. 11 786 091.6, filed on May 25, 2011, 9 pages.

International Search Report mailed on Sep. 8, 2011, for PCT Patent Application No. PCT/CN2011/074678, filed on May 25, 2011, 8 pages.

International Search Report mailed on Dec. 8, 2011, for PCT Patent Application No. PCT/CN2011/079143, filed on Aug. 31, 2011, 5 pages.

Lazar, E. et al. (Mar. 1988). "Transforming Growth Factor α: Mutation of Aspartic Acid 47 and Leucine 48 Results in Different Biological Activities," *Mol. Cellular Biology* 8(3):1247-1252.

Li, Z.X. et al. (2006). "The Progress of Study on Granulocyte Colony-Stimulating Factor," *J. Int'l Neurology and Neurosurgery* 33(1):79-82 (English Abstract Only).

Matsueda, G.R. et al. (Oct. 1, 1979). "Increased Efficiency in Solid-Phase Edman Degradation of Synthetic Peptidyl-Resins Using an Oxymethylphenylacetamidomethyl-Linkage," *FEBS Letters* 106(1):89-92.

Sierra, J. et al. (Jul. 10, 2008). "A Single Dose of Pegfilgrastim Compared With Daily Filgrastim for Supporting Neutrophil Recovery in Patients Treated for Low-to-Intermediate Risk Acute Myeloid Lukemia: Results from a Randomized, Double-Blind, Phase 2 Trial," *BMC Cancer* 8:195.

Solaroglu, I. et al. (Apr. 1, 2006; e-pub. Mar. 2, 2006). "A Novel Neuroprotectant Granulocyte-Colony Stimulating Factor," *Stroke* 37(4):1123-1128.

Tao, H.Z. et al. (Dec. 4-7, 2010). "F-627, a G-CSF Dimer, Stimulated a More Rapid Neutrophil Recovery in Cyclophosphamide-Treated Monkeys Compared to Monomer Rhg-CSFs," Annual Meeting of the American Society of Hematology (ASH), Orlando, FL., 2 pages.

Vidarsson, G. et al. (2001). "Activity of human IgG and IgA subclasses in immune defense against Neisseria meningitidis serogroup B," *J. Immunol.* 166(10):6250-6256.

Written Opinion of the International Searching Authority mailed on Sep. 8, 2011, for PCT Patent Application No. PCT/CN2011/074678, filed on May 25, 2011, 7 pages.

Written Opinion of the International Searching Authority mailed on Dec. 8, 2011, for PCT Patent Application No. PCT/CN2011/079143, filed on Aug. 31, 2011, 12 pages.

Wu, C. et al. (Nov. 2007; e-pub. Oct. 14, 2007). "Simultaneous Targeting of Multiple Disease Mediators by a Dual-Variable-Domain Immunoglobulin," *Nature Biotech.* 25(11):1290-1297.

Xiao, B.G. et al. (Nov. 1, 2007). "Cell Biology and Clinical Promise of G-CSF: Immunomodulation and Neuroprotection," *J. Cellular and Molecular Medicine* 11(6):1272-1290.

(56) References Cited

OTHER PUBLICATIONS

Zhu, Q. et al. (Nov. 25, 2008). "Expression of rhEPO-L-Fc Fusion Protein and Analysis of its Bioactivity and Pharmacokinetics," *Chinese J. Biotech.* 24(11):1874-1879 (English Translation of Abstract Only).

European Office Action mailed on May 29, 2015, for European Patent Application No. 11 821 119.2, filed on May 25, 2011, 10 pages.

Bork, P. (2000). "Powers and Pitfalls in Sequence Analysis: The 70% Hurdle" *Genome Research* 10:398-400.

Wu, C. (2010). "Generation and Characterization of a Dual Variable Domain Immunoglobulin (DVD-Ig™) Molecule" Chapter 19 in *Antibody Engineering*. vol. 2. Second Ed., Springer-Verlag Berlin, Heidelberg; pp. 240-250.

Wu, C. et al. (Jul. 2009). "Molecular construction and optimization of anti-human IL-1α/β dual variable domain immunoglobulin (DVD-Ig™) molecules," *Landes Bioscience*: 339-347.

Extended European Search Report dated Mar. 30, 2016, for European Patent Application No. 15 188 775.9, filed on May 25, 2011, 28 pages.

Belayev, L. et al. (Nov. 11, 1996). "Quantitative Evaluation of Blood-Brain Barrier Permeability Following Middle Cerebral Artery Occlusion in Rats," *Brain Research* 739(1-2):88-96.

Ding-Zhou, L. et al. (Dec. 2002). "L-Name Reduces Infarction, Neurological Deficit and Blood—Brain Barrier Disruption Following Cerebral lschemia in Mice," *European Journal of Pharmacology* 457(2-3):137-146.

Halpern, W. et al. (Nov. 2002). "Albugranin™, a Recombinant Human Granulocyte Colony Stimulating Factor (G-CSF) Genetically Fused to Recombinant Human Albumin Induces Prolonged Myelopoietic Effects in Mice and Monkeys," *Pharmaceutical Research* 19(11):1720-1729.

Sood, R. et al. (Feb. 2008; E-published on Aug. 15, 2007). "Early Beneficial Effect of Matrix Metalloproteinase Inhibition on BBB Permeability as Measured by MRI Countered by Impaired Long-Term Recovery After Stroke in Rat Brain," *J Cereb Blood Flow Metab.* 28(2):431-438.

\* cited by examiner

SEQUENCE LISTING

```
<160> NUMBER OF SEQ ID NOS: 13

<210> SEQ ID NO 1
<211> LENGTH: 364
<212> TYPE: PRT
<213> ORGANISM: Artificial Sequence
<220> FEATURE:
```

<223> OTHER INFORMATION: G-CSF Dimer

<400> SEQUENCE: 1

```
Thr Pro Leu Gly Pro Ala Ser Ser Leu Pro Gln Ser Phe Leu Leu Lys
 1               5                  10                  15

Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro Gly Ser
                165                 170                 175

Gly Gly Gly Ser Gly Gly Gly Ser Gly Gly Gly Ser Thr Pro
            180                 185                 190

Leu Gly Pro Ala Ser Ser Leu Pro Gln Ser Phe Leu Leu Lys Cys Leu
    195                 200                 205

Glu Gln Val Arg Lys Ile Gln Gly Asp Gly Ala Ala Leu Gln Glu Lys
210                 215                 220

Leu Cys Ala Thr Tyr Lys Leu Cys His Pro Glu Glu Leu Val Leu Leu
225                 230                 235                 240

Gly His Ser Leu Gly Ile Pro Trp Ala Pro Leu Ser Ser Cys Pro Ser
                245                 250                 255

Gln Ala Leu Gln Leu Ala Gly Cys Leu Ser Gln Leu His Ser Gly Leu
            260                 265                 270

Phe Leu Tyr Gln Gly Leu Leu Gln Ala Leu Glu Gly Ile Ser Pro Glu
        275                 280                 285

Leu Gly Pro Thr Leu Asp Thr Leu Gln Leu Asp Val Ala Asp Phe Ala
    290                 295                 300

Thr Thr Ile Trp Gln Gln Met Glu Glu Leu Gly Met Ala Pro Ala Leu
305                 310                 315                 320

Gln Pro Thr Gln Gly Ala Met Pro Ala Phe Ala Ser Ala Phe Gln Arg
                325                 330                 335

Arg Ala Gly Gly Val Leu Val Ala Ser His Leu Gln Ser Phe Leu Glu
            340                 345                 350

Val Ser Tyr Arg Val Leu Arg His Leu Ala Gln Pro
        355                 360
```

<210> SEQ ID NO 2
<211> LENGTH: 418
<212> TYPE: PRT
<213> ORGANISM: Artificial Sequence
<220> FEATURE:

<223> OTHER INFORMATION: G-CSF monomer having Fc fragment

<400> SEQUENCE: 2

```
Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
            85                  90                  95

Pro Glu Leu Gly Pro Thr Leu Asp Thr Leu Gln Leu Asp Val Ala Asp
        100                 105                 110

Phe Ala Thr Thr Ile Trp Gln Gln Met Glu Glu Leu Gly Met Ala Pro
    115                 120                 125

Ala Leu Gln Pro Thr Gln Gly Ala Met Pro Ala Phe Ala Ser Ala Phe
130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro Gly Ser
            165                 170                 175

Gly Gly Gly Ser Gly Gly Gly Ser Gly Gly Gly Ser Glu Arg
        180                 185                 190

Lys Cys Cys Val Glu Cys Pro Pro Cys Pro Ala Pro Pro Val Ala Gly
    195                 200                 205

Pro Ser Val Phe Leu Phe Pro Pro Lys Pro Lys Asp Thr Leu Met Ile
210                 215                 220

Ser Arg Thr Pro Glu Val Thr Cys Val Val Val Asp Val Ser His Glu
225                 230                 235                 240

Asp Pro Glu Val Gln Phe Asn Trp Tyr Val Asp Gly Val Glu Val His
            245                 250                 255

Asn Ala Lys Thr Lys Pro Arg Glu Glu Gln Phe Asn Ser Thr Phe Arg
        260                 265                 270

Val Val Ser Val Leu Thr Val Val His Gln Asp Trp Leu Asn Gly Lys
    275                 280                 285

Glu Tyr Lys Cys Lys Val Ser Asn Lys Gly Leu Pro Ala Ser Ile Glu
290                 295                 300

Lys Thr Ile Ser Lys Thr Lys Gly Gln Pro Arg Glu Pro Gln Val Tyr
305                 310                 315                 320

Thr Leu Pro Pro Ser Arg Glu Glu Met Thr Lys Asn Gln Val Ser Leu
            325                 330                 335

Thr Cys Leu Val Lys Gly Phe Tyr Pro Ser Asp Ile Ala Val Glu Trp
        340                 345                 350

Glu Ser Asn Gly Gln Pro Glu Asn Asn Tyr Lys Thr Thr Pro Pro Met
    355                 360                 365

Leu Asp Ser Asp Gly Ser Phe Phe Leu Tyr Ser Lys Leu Thr Val Asp
370                 375                 380

Lys Ser Arg Trp Gln Gln Gly Asn Val Phe Ser Cys Ser Val Met His
385                 390                 395                 400
```

-continued

Glu Ala Leu His Asn His Tyr Thr Gln Lys Ser Leu Ser Leu Ser Pro
                        405                 410                 415

Gly Lys

<210> SEQ ID NO 3
<211> LENGTH: 418
<212> TYPE: PRT
<213> ORGANISM: Artificial Sequence
<220> FEATURE:
<223> OTHER INFORMATION: G-CSF monomer having Fc fragment

<400> SEQUENCE: 3

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val His Gln Asp Trp Leu Asn
                85                  90                  95

Gly Lys Glu Tyr Lys Cys Lys Val Ser Asn Lys Gly Leu Pro Ala Ser
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys Gly Ser Gly Gly Ser Gly Gly Gly Ser
225                 230                 235                 240

Gly Gly Gly Ser Thr Pro Leu Gly Pro Ala Ser Ser Leu Pro Gln Ser
            245                 250                 255

Phe Leu Leu Lys Cys Leu Glu Gln Val Arg Lys Ile Gln Gly Asp Gly
        260                 265                 270

Ala Ala Leu Gln Glu Lys Leu Cys Ala Thr Tyr Lys Leu Cys His Pro
    275                 280                 285

Glu Glu Leu Val Leu Leu Gly His Ser Leu Gly Ile Pro Trp Ala Pro
    290                 295                 300

Leu Ser Ser Cys Pro Ser Gln Ala Leu Gln Leu Ala Gly Cys Leu Ser
305                 310                 315                 320

Gln Leu His Ser Gly Leu Phe Leu Tyr Gln Gly Leu Leu Gln Ala Leu
                325                 330                 335

Glu Gly Ile Ser Pro Glu Leu Gly Pro Thr Leu Asp Thr Leu Gln Leu

```
              340                 345                 350
Asp Val Ala Asp Phe Ala Thr Thr Ile Trp Gln Gln Met Glu Glu Leu
            355                 360                 365
Gly Met Ala Pro Ala Leu Gln Pro Thr Gln Gly Ala Met Pro Ala Phe
        370                 375                 380
Ala Ser Ala Phe Gln Arg Arg Ala Gly Gly Val Leu Val Ala Ser His
385                 390                 395                 400
Leu Gln Ser Phe Leu Glu Val Ser Tyr Arg Val Leu Arg His Leu Ala
                405                 410                 415
Gln Pro

<210> SEQ ID NO 4
<211> LENGTH: 403
<212> TYPE: PRT
<213> ORGANISM: Artificial Sequence
<220> FEATURE:
<223> OTHER INFORMATION: G-CSF monomer having Fc fragment

<400> SEQUENCE: 4

Thr Pro Leu Gly Pro Ala Ser Ser Leu Pro Gln Ser Phe Leu Leu Lys
1               5                   10                  15
Cys Leu Glu Gln Val Arg Lys Ile Gln Gly Asp Gly Ala Ala Leu Gln
            20                  25                  30
Glu Lys Leu Cys Ala Thr Tyr Lys Leu Cys His Pro Glu Glu Leu Val
        35                  40                  45
Leu Leu Gly His Ser Leu Gly Ile Pro Trp Ala Pro Leu Ser Ser Cys
    50                  55                  60
Pro Ser Gln Ala Leu Gln Leu Ala Gly Cys Leu Ser Gln Leu His Ser
65                  70                  75                  80
Gly Leu Phe Leu Tyr Gln Gly Leu Leu Gln Ala Leu Glu Gly Ile Ser
                85                  90                  95
Pro Glu Leu Gly Pro Thr Leu Asp Thr Leu Gln Leu Asp Val Ala Asp
            100                 105                 110
Phe Ala Thr Thr Ile Trp Gln Gln Met Glu Glu Leu Gly Met Ala Pro
        115                 120                 125
Ala Leu Gln Pro Thr Gln Gly Ala Met Pro Ala Phe Ala Ser Ala Phe
    130                 135                 140
Gln Arg Arg Ala Gly Gly Val Leu Val Ala Ser His Leu Gln Ser Phe
145                 150                 155                 160
Leu Glu Val Ser Tyr Arg Val Leu Arg His Leu Ala Gln Pro Ala Ser
                165                 170                 175
Thr Lys Gly Pro Val Glu Cys Pro Pro Cys Pro Ala Pro Pro Val Ala
            180                 185                 190
Gly Pro Ser Val Phe Leu Phe Pro Pro Lys Pro Lys Asp Thr Leu Met
        195                 200                 205
Ile Ser Arg Thr Pro Glu Val Thr Cys Val Val Val Asp Val Ser His
    210                 215                 220
Glu Asp Pro Glu Val Gln Phe Asn Trp Tyr Val Asp Gly Val Glu Val
225                 230                 235                 240
His Asn Ala Lys Thr Lys Pro Arg Glu Glu Gln Phe Asn Ser Thr Phe
                245                 250                 255
Arg Val Val Ser Val Leu Thr Val Val His Gln Asp Trp Leu Asn Gly
            260                 265                 270
Lys Glu Tyr Lys Cys Lys Val Ser Asn Lys Gly Leu Pro Ala Ser Ile
        275                 280                 285
```

```
Glu Lys Thr Ile Ser Lys Thr Lys Gly Gln Pro Arg Glu Pro Gln Val
    290                 295                 300
Tyr Thr Leu Pro Pro Ser Arg Glu Glu Met Thr Lys Asn Gln Val Ser
305                 310                 315                 320
Leu Thr Cys Leu Val Lys Gly Phe Tyr Pro Ser Asp Ile Ala Val Glu
                325                 330                 335
Trp Glu Ser Asn Gly Gln Pro Glu Asn Asn Tyr Lys Thr Thr Pro Pro
                340                 345                 350
Met Leu Asp Ser Asp Gly Ser Phe Phe Leu Tyr Ser Lys Leu Thr Val
            355                 360                 365
Asp Lys Ser Arg Trp Gln Gln Gly Asn Val Phe Ser Cys Ser Val Met
        370                 375                 380
His Glu Ala Leu His Asn His Tyr Thr Gln Lys Ser Leu Ser Leu Ser
385                 390                 395                 400
Pro Gly Lys

<210> SEQ ID NO 5
<211> LENGTH: 403
<212> TYPE: PRT
<213> ORGANISM: Artificial Sequence
<220> FEATURE:
<223> OTHER INFORMATION: G-CSF monomer having Fc fragment

<400> SEQUENCE: 5

Val Glu Cys Pro Pro Cys Pro Ala Pro Pro Val Ala Gly Pro Ser Val
  1               5                  10                  15
Phe Leu Phe Pro Pro Lys Pro Lys Asp Thr Leu Met Ile Ser Arg Thr
                 20                  25                  30
Pro Glu Val Thr Cys Val Val Val Asp Val Ser His Glu Asp Pro Glu
             35                  40                  45
Val Gln Phe Asn Trp Tyr Val Asp Gly Val Glu Val His Asn Ala Lys
         50                  55                  60
Thr Lys Pro Arg Glu Glu Gln Phe Asn Ser Thr Phe Arg Val Val Ser
 65                  70                  75                  80
Val Leu Thr Val Val His Gln Asp Trp Leu Asn Gly Lys Glu Tyr Lys
                 85                  90                  95
Cys Lys Val Ser Asn Lys Gly Leu Pro Ala Ser Ile Glu Lys Thr Ile
            100                 105                 110
Ser Lys Thr Lys Gly Gln Pro Arg Glu Pro Gln Val Tyr Thr Leu Pro
        115                 120                 125
Pro Ser Arg Glu Glu Met Thr Lys Asn Gln Val Ser Leu Thr Cys Leu
    130                 135                 140
Val Lys Gly Phe Tyr Pro Ser Asp Ile Ala Val Glu Trp Glu Ser Asn
145                 150                 155                 160
Gly Gln Pro Glu Asn Asn Tyr Lys Thr Thr Pro Pro Met Leu Asp Ser
                165                 170                 175
Asp Gly Ser Phe Phe Leu Tyr Ser Lys Leu Thr Val Asp Lys Ser Arg
            180                 185                 190
Trp Gln Gln Gly Asn Val Phe Ser Cys Ser Val Met His Glu Ala Leu
        195                 200                 205
His Asn His Tyr Thr Gln Lys Ser Leu Ser Leu Ser Pro Gly Lys Ala
    210                 215                 220
Ser Thr Lys Gly Pro Thr Pro Leu Gly Pro Ala Ser Ser Leu Pro Gln
225                 230                 235                 240
```

-continued

```
Ser Phe Leu Leu Lys Cys Leu Glu Gln Val Arg Lys Ile Gln Gly Asp
            245                 250                 255

Gly Ala Ala Leu Gln Glu Lys Leu Cys Ala Thr Tyr Lys Leu Cys His
        260                 265                 270

Pro Glu Glu Leu Val Leu Leu Gly His Ser Leu Gly Ile Pro Trp Ala
    275                 280                 285

Pro Leu Ser Ser Cys Pro Ser Gln Ala Leu Gln Leu Ala Gly Cys Leu
290                 295                 300

Ser Gln Leu His Ser Gly Leu Phe Leu Tyr Gln Gly Leu Leu Gln Ala
305                 310                 315                 320

Leu Glu Gly Ile Ser Pro Glu Leu Gly Pro Thr Leu Asp Thr Leu Gln
            325                 330                 335

Leu Asp Val Ala Asp Phe Ala Thr Thr Ile Trp Gln Gln Met Glu Glu
        340                 345                 350

Leu Gly Met Ala Pro Ala Leu Gln Pro Thr Gln Gly Ala Met Pro Ala
    355                 360                 365

Phe Ala Ser Ala Phe Gln Arg Arg Ala Gly Gly Val Leu Val Ala Ser
370                 375                 380

His Leu Gln Ser Phe Leu Glu Val Ser Tyr Arg Val Leu Arg His Leu
385                 390                 395                 400

Ala Gln Pro

<210> SEQ ID NO 6
<211> LENGTH: 413
<212> TYPE: PRT
<213> ORGANISM: Artificial Sequence
<220> FEATURE:
<223> OTHER INFORMATION: G-CSF monomer having Fc fragment

<400> SEQUENCE: 6

Thr Pro Leu Gly Pro Ala Ser Ser Leu Pro Gln Ser Phe Leu Leu Lys
  1               5                  10                  15

Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro Gly Ser
                165                 170                 175

Gly Gly Gly Ser Gly Gly Gly Gly Ser Gly Gly Gly Ser Val Glu
            180                 185                 190

Cys Pro Pro Cys Pro Ala Pro Pro Val Ala Gly Pro Ser Val Phe Leu
```

```
                195                 200                 205
Phe Pro Pro Lys Pro Lys Asp Thr Leu Met Ile Ser Arg Thr Pro Glu
    210                 215                 220

Val Thr Cys Val Val Val Asp Val Ser His Glu Asp Pro Glu Val Gln
225                 230                 235                 240

Phe Asn Trp Tyr Val Asp Gly Val Glu Val His Asn Ala Lys Thr Lys
                245                 250                 255

Pro Arg Glu Glu Gln Phe Asn Ser Thr Phe Arg Val Val Ser Val Leu
            260                 265                 270

Thr Val Val His Gln Asp Trp Leu Asn Gly Lys Glu Tyr Lys Cys Lys
        275                 280                 285

Val Ser Asn Lys Gly Leu Pro Ala Ser Ile Glu Lys Thr Ile Ser Lys
    290                 295                 300

Thr Lys Gly Gln Pro Arg Glu Pro Gln Val Tyr Thr Leu Pro Pro Ser
305                 310                 315                 320

Arg Glu Glu Met Thr Lys Asn Gln Val Ser Leu Thr Cys Leu Val Lys
                325                 330                 335

Gly Phe Tyr Pro Ser Asp Ile Ala Val Glu Trp Glu Ser Asn Gly Gln
            340                 345                 350

Pro Glu Asn Asn Tyr Lys Thr Thr Pro Pro Met Leu Asp Ser Asp Gly
        355                 360                 365

Ser Phe Phe Leu Tyr Ser Lys Leu Thr Val Asp Lys Ser Arg Trp Gln
    370                 375                 380

Gln Gly Asn Val Phe Ser Cys Ser Val Met His Glu Ala Leu His Asn
385                 390                 395                 400

His Tyr Thr Gln Lys Ser Leu Ser Leu Ser Pro Gly Lys
                405                 410

<210> SEQ ID NO 7
<211> LENGTH: 413
<212> TYPE: PRT
<213> ORGANISM: Artificial Sequence
<220> FEATURE:
<223> OTHER INFORMATION: G-CSF monomer having Fc fragment

<400> SEQUENCE: 7

Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
                20                  25                  30

Pro Glu Val Thr Cys Val Val Val Asp Val Ser His Glu Asp Pro Glu
            35                  40                  45

Val Gln Phe Asn Trp Tyr Val Asp Gly Val Glu Val His Asn Ala Lys
        50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Ser Ile Glu Lys Thr Ile
            100                 105                 110

Ser Lys Thr Lys Gly Gln Pro Arg Glu Pro Gln Val Tyr Thr Leu Pro
        115                 120                 125

Pro Ser Arg Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
```

```
                145                 150                 155                 160
Gly Gln Pro Glu Asn Asn Tyr Lys Thr Thr Pro Pro Met Leu Asp Ser
                    165                 170                 175

Asp Gly Ser Phe Phe Leu Tyr Ser Lys Leu Thr Val Asp Lys Ser Arg
                    180                 185                 190

Trp Gln Gly Asn Val Phe Ser Cys Ser Val Met His Glu Ala Leu
                    195                 200                 205

His Asn His Tyr Thr Gln Lys Ser Leu Ser Leu Ser Pro Gly Lys Gly
            210                 215                 220

Ser Gly Gly Gly Ser Gly Gly Gly Ser Gly Gly Gly Ser Thr
225                 230                 235                 240

Pro Leu Gly Pro Ala Ser Ser Leu Pro Gln Ser Phe Leu Leu Lys Cys
                    245                 250                 255

Leu Glu Gln Val Arg Lys Ile Gln Gly Asp Gly Ala Ala Leu Gln Glu
                    260                 265                 270

Lys Leu Cys Ala Thr Tyr Lys Leu Cys His Pro Glu Glu Leu Val Leu
                    275                 280                 285

Leu Gly His Ser Leu Gly Ile Pro Trp Ala Pro Leu Ser Ser Cys Pro
            290                 295                 300

Ser Gln Ala Leu Gln Leu Ala Gly Cys Leu Ser Gln Leu His Ser Gly
305                 310                 315                 320

Leu Phe Leu Tyr Gln Gly Leu Leu Gln Ala Leu Glu Gly Ile Ser Pro
                    325                 330                 335

Glu Leu Gly Pro Thr Leu Asp Thr Leu Gln Leu Asp Val Ala Asp Phe
                    340                 345                 350

Ala Thr Thr Ile Trp Gln Gln Met Glu Glu Leu Gly Met Ala Pro Ala
                    355                 360                 365

Leu Gln Pro Thr Gln Gly Ala Met Pro Ala Phe Ala Ser Ala Phe Gln
                    370                 375                 380

Arg Arg Ala Gly Gly Val Leu Val Ala Ser His Leu Gln Ser Phe Leu
385                 390                 395                 400

Glu Val Ser Tyr Arg Val Leu Arg His Leu Ala Gln Pro
                    405                 410

<210> SEQ ID NO 8
<211> LENGTH: 174
<212> TYPE: PRT
<213> ORGANISM: Artificial Sequence
<220> FEATURE:
<223> OTHER INFORMATION: G-CSF monomer

<400> SEQUENCE: 8

Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
                20                  25                  30

Glu Lys Leu Cys Ala Thr Tyr Lys Leu Cys His Pro Glu Glu Leu Val
                35                  40                  45

Leu Leu Gly His Ser Leu Gly Ile Pro Trp Ala Pro Leu Ser Ser Cys
            50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
```

```
            100                 105                 110
Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170
```

<210> SEQ ID NO 9
<211> LENGTH: 1368
<212> TYPE: DNA
<213> ORGANISM: Artificial Sequence
<220> FEATURE:
<223> OTHER INFORMATION: Fc fragments with sequences encoding G-CSF
      monomer

<400> SEQUENCE: 9

```
aagcttccca gacccatggc tggacctgcc acccagagcc ccatgaagct gatggccctg      60
cagctgctgc tgtggcacag tgcactctgg acagtgcagg aagccacccc cctgggccct     120
gccagctccc tgccccagag cttcctgctc aagtgcttag agcaagtgag gaagatccag     180
ggcgatggcg cagcgctcca ggagaagctg tgtgccacct acaagctgtg ccaccccgag     240
gagctggtgc tgctcggaca ctctctgggc atccctggg ctcccctgag cagctgcccc     300
agccaggccc tgcagctggc aggctgcttg agccaactcc atagcggcct tttcctctac     360
caggggctcc tgcaggccct ggaagggatc tccccgagt tgggtccac cttggacaca     420
ctgcagctgg acgtcgccga ctttgccacc accatctggc agcagatgga agaactggga     480
atggcccctg ccctgcagcc cacccagggt gccatgccgg ccttcgcctc tgctttccag     540
cgccgggcag gagggtcct ggttgcctcc atctgcaga gcttcctgga ggtgtcgtac     600
cgcgttctac gccaccttgc ccagcccgga tccggtggcg gttccggtgg aggcggaagc     660
ggcggtggag gatcagagcg caaatgttgt gtcgagtgcc caccgtgccc agcaccacct     720
gtggcaggac cgtcagtctt cctcttcccc ccaaaaccca aggacaccct catgatctcc     780
cggacccctg aggtcacgtg cgtggtggtg gacgtgagcc acgaagaccc cgaggtccag     840
ttcaactggt acgtgacgg cgtggaggtg cataatgcca agacaaagcc acgggaggag     900
cagttcaaca gcacgttccg tgtggtcagc gtcctcaccg ttgtgcacca ggactggctg     960
aacggcaagg agtacaagtg caaggtctcc aacaaaggcc tcccagcctc catcgagaaa    1020
accatctcca aaaccaaagg gcagccccga gaaccacagg tgtacaccct gcccccatcc    1080
cgggaggaga tgaccaagaa ccaggtcagc ctgacctgcc tggtcaaagg cttctacccc    1140
agcgacatcg ccgtggagtg ggagagcaat gggcagccgg agaacaacta caagaccaca    1200
cctcccatgc tggactccga cggctccttc ttcctctaca gcaagctcac cgtggacaag    1260
agcaggtggc agcaggggaa cgtcttctca tgctccgtga tgcatgaggc tctgcacaac    1320
cactacacgc agaagagcct ctccctgtct ccgggtaaat gagaattc                  1368
```

<210> SEQ ID NO 10
<211> LENGTH: 1353
<212> TYPE: DNA
<213> ORGANISM: Artificial Sequence
<220> FEATURE:
<223> OTHER INFORMATION: Fc fragments with sequences encoding G-CSF
      monomer

<400> SEQUENCE: 10

```
aagcttccca gacccatggc tggacctgcc acccagagcc ccatgaagct gatggccctg      60
cagctgctgc tgtggcacag tgcactctgg acagtgcagg aagccacccc cctgggccct     120
gccagctccc tgccccagag cttcctgctc aagtgcttag agcaagtgag gaagatccag     180
ggcgatggcg cagcgctcca ggagaagctg tgtgccacct acaagctgtg ccaccccgag     240
gagctggtgc tgctcggaca ctctctgggc atcccctggg ctcccctgag cagctgcccc     300
agccaggccc tgcagctggc aggctgcttg agccaactcc atagcggcct tttcctctac     360
caggggctcc tgcaggccct ggaagggatc tcccccgagt tgggtcccac cttggacaca     420
ctgcagctgg acgtcgccga ctttgccacc accatctggc agcagatgga agaactggga     480
atggcccctg ccctgcagcc cacccagggt gccatgccgg ccttcgcctc tgctttccag     540
cgccgggcag aggggtcct ggttgcctcc catctgcaga gcttcctgga ggtgtcgtac      600
cgcgttctac gccaccttgc ccagcccgga tccggtggcg gttccggtgg aggcggaagc     660
ggcggtggag gatcagtcga gtgcccaccg tgcccagcac acctgtggc aggaccgtca      720
gtcttcctct ccccccaaa acccaaggac accctcatga tctcccggac ccctgaggtc      780
acgtgcgtgg tggtggacgt gagccacgaa gaccccgagg tccagttcaa ctggtacgtg     840
gacggcgtgg aggtgcataa tgccaagaca aagccacggg aggagcagtt caacagcacg     900
ttccgtgtgg tcagcgtcct caccgttgtg caccaggact ggctgaacgg caaggagtac     960
aagtgcaagg tctccaacaa aggcctccca gcctccatcg agaaaaccat ctccaaaacc    1020
aaagggcagc cccgagaacc acaggtgtac accctgcccc catcccggga ggagatgacc    1080
aagaaccagg tcagcctgac ctgcctggtc aaaggcttct accccagcga catcgccgtg    1140
gagtgggaga gcaatgggca gccggagaac aactacaaga ccacacctcc catgctggac    1200
tccgacggct ccttcttcct ctacagcaag ctcaccgtgg acaagagcag gtggcagcag    1260
gggaacgtct tctcatgctc cgtgatgcat gaggctctgc acaaccacta cacgcagaag    1320
agcctctccc tgtctccggg taaatgagaa ttc                                 1353
```

<210> SEQ ID NO 11
<211> LENGTH: 6
<212> TYPE: PRT
<213> ORGANISM: Artificial Sequence
<220> FEATURE:
<223> OTHER INFORMATION: Synthetic Construct

<400> SEQUENCE: 11

Gly Pro Gly Pro Gly Pro
1               5

<210> SEQ ID NO 12
<211> LENGTH: 4
<212> TYPE: PRT
<213> ORGANISM: Artificial Sequence
<220> FEATURE:
<223> OTHER INFORMATION: Synthetic Construct

<400> SEQUENCE: 12

Gly Ser Gly Gly
1

<210> SEQ ID NO 13
<211> LENGTH: 17
<212> TYPE: PRT

```
<213> ORGANISM: Artificial Sequence
<220> FEATURE:
<223> OTHER INFORMATION: Synthetic Construct

<400> SEQUENCE: 13

Thr Gly Leu Gln Pro Thr Arg Gly Ile Asp Asp Ile Thr Ser Pro Val
1               5                   10                  15

Asp
```

USE OF G-CSF DIMER IN PREPARATION OF MEDICAMENT FOR TREATMENT OF NEURODEGENERATIVE DISEASES

CROSS-REFERENCE TO RELATED APPLICATIONS

This application is a National Phase application under 35 U.S.C. §371 of International Application No. PCT/CN2012/079106, filed Jul. 24, 2012 and claims benefit of Chinese Application No. 201110209712.0, filed Jul. 25, 2011, the disclosures of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 720622000500SequenceListing.txt, date recorded: Jul. 1, 2015, size: 28,532 bytes). No new matter is added.

FIELD OF THE INVENTION

The invention relates to the fields of biology and medicine. More particularly, the invention relates to a new G-CSF dimer and its use in the treatment of neurodegenerative diseases.

BACKGROUND OF INVENTION

Human granulocyte colony-stimulating factor (G-CSF) is a glycoprotein containing 204 amino acids with 30 amino-acid signal peptides. Mature G-CSF protein, having a molecular weight of 18-20 kDa, is composed of 174 amino acids without signal peptides and secreted out of the cells. Human cells mainly responsible for such secretion are monocytes, fibroblasts, and endothelial cells.

There are three main biological functions for G-CSF in vivo, namely:

acting on neutrophil precursor cells and bone marrow stem cells. Actuating the polarization, proliferation and maturation of neutrophilic granulocyte.

activating the mature neutrophilic granulocyte to participate in immune response, and cooperating with other hematopoietic growth factors, such as Stem Cell Factor, Flt-3 ligand, and GM-CSF to exert hematopoietic functions.

G-CSF Receptor (G-CSFR) is proven to exist mainly in bone marrow hematopoietic stem cells Sca+Lin-Th1low, precursor cells CD34+, committed granulocyte precursor cells, and mature neutrophils. G-CSFR is a specific receptor having a high affinity to G-CSF and is composed of 812 amino acids.

Tamada et al. obtained the crystalline structure of the G-CSF: G-CSFR complex and the stoichiometry of G-CSF: G-CSFR complex was shown as a 2:2 ratio by the 2.8 angstrom diffraction analysis (PNAS, 2008, Vol. 103: 3135-3140), i.e., a complex comprises 2 ligands and 2 receptors bound together. In other words, in each complex, each G-CSF molecule binds to one receptor chain molecule; when both G-CSF molecules are bound with G-CSFRs, they are brought to close proximity and a 2:2 dimer is formed as a result of this interaction. Under this circumstance, the carboxyl terminal of the G-CSF receptor is then able to activate the downstream signal molecules Janus tyrosine kinases JAK2. JAK2 then stimulates cell differentiation and proliferation by activating STAT3 to switch on gene transcription.

In 2003, Schabitz W. R. et al. reported that recombinant human G-CSF was shown to have a protective functionality on nerve cells in the ischemic animal model (Storke, 2003, 34; 745-751). In 2006, Shyu et al. reported that rhG-CSF was shown to have clinical efficacy in the treatment of patients having acute stroke in which the patients were administered with rhG-CSF daily for five consecutive days (CMAJ, 2006, 174:927-933). The in vivo half-life of G-CSF in rat upon subcutaneous administration is about 2 hr, whereas the half-life of G-CSF in human upon subcutaneous administration is only 3.5 hr. Therefore, patients needed to be administered with the drug on a daily basis, and this affected the living quality of patients.

Neurodegenerative disease is a condition of neuronal loss in brain and spinal cord. It is a kind of chronic and progressive disease of the nervous system, mainly including Alzheimer's disease (AD), Parkinson's disease (PD), Huntington disease, amyotrophic lateral sclerosis, spinal muscular atrophy, and spinal cerebellar ataxias, etc. These neurological diseases are characterized by a common feature of degeneration and apoptosis of neurons, which result in the abnormal behavior and dysfunction of patients, and lead to a premature death. The pathogenesis of neurodegenerative diseases remains obscure, as yet no existing effective method and medicine are available. Current treatments for PD comprise the replenishment of the substances deficient neurons in patients' brain via oral administration or intravenous injection, such as levodopa, whereas levodopa cannot efficiently control the naturally pathogenic progression of PD and cannot affect the speed of degeneration of dopaminergic neurons. Moreover, use of levodopa brings adverse side effects, such as on-off phenomenon and dyskinesia, and its therapeutic effects only last about 2 years. Long-term use of levodopa may cause neuronal damage as well as apoptosis of the neurons. Current treatments for AD comprise increasing the concentration of acetylcholine directed against the deficiency of acetylcholine in AD patients' brain. This method cannot control the development of the disease, either.

At present, medicines for treating PD are mostly to reduce symptoms, such as dopamine replacers (levodopa or dopamine agonists). Among them, levodopa (L-DOPA) supplements dopamine in the brain as a precursor of dopamine, which is the most commonly used and effective therapy for PD. However, long-term usage of such drug may easily reduce the curative effect and bring serious side effects, even an on-off phenomenon. In addition, prevention of the loss of dopaminergic neurons is also one of the main strategies for the treatment of PD, in which neurotrophic factor (GDNF) is studied the most currently. However, GDNF was not shown to exhibit efficacy but a series of side effects in the clinical trials, such as nausea, anorexia, and weight loss, etc. (Neurology, 2003, 69:69-73). Use of G-CSF in the treatment of PD has also been reported. However, in both animal models of PD and clinical trials, the administration dosage of G-CSF is high, the therapeutic response is slow, and more frequent administration and longer treatment duration are needed, resulting in a reduction of patient compliance and making it inconvenient for the patients to use the drug.

Therefore, there is an urgent need in the art to develop more effective drugs for treatment of neurodegenerative diseases.

SUMMARY OF INVENTION

It is an object of the present invention to provide a drug for the treatment of neurodegenerative diseases with improved efficacy and the manufacture and use thereof.

In one aspect of the present invention, a use of G-CSF dimer in the manufacture of a composition for treatment or prevention of a neurodegenerative disease is provided.

The neurodegenerative disease is selected from Parkinson's disease, Alzheimer's disease, Huntington disease, amyotrophic lateral sclerosis, spinal muscular atrophy, primary lateral sclerosis, and spinal cerebellar ataxias.

The G-CSF dimer is a human G-CSF dimer.

According to the present invention, the structure of G-CSF dimer is shown as formula I:

$$M1-L-M2 \qquad \qquad I$$

wherein M1 is a first monomer of human G-CSF; M2 is a second monomer of human G-CSF; and L is a linker connecting said first monomer and said second monomer and disposed therebetween.

Also, the G-CSF dimer retains the biological activity of G-CSF monomer and has a serum half-life of longer than twice of that of either the first or the second monomer.

Further, the linker L is selected from the group consisting of:
(i) a short peptide comprising 3 to 50 amino acids; and
(ii) a polypeptide of formula II:

$$-Z-Y-Z- \qquad \qquad II$$

wherein Y is a carrier protein; Z is nothing, or a short peptide comprising 1 to 30 amino acids. "-" is a chemical bond or a covalent bond. Preferably, "-" is a peptide bond.

In another preferred embodiment, the amino acid sequence of human G-CSF dimer herein is shown as SEQ ID NO: 1.

In another preferred embodiment, the first monomer and the second monomer are identical. The amino acid sequence of the first monomer and the second monomer is shown as SEQ ID NO: 8.

According to the present invention, the amino acid of human G-CSF dimer is produced by two G-CSF-Fc complexes (a G-CSF-Fc complex is a G-CSF monomer with a Fc fragment). In a preferred embodiment, the G-CSF-Fc complex comprises an amino acid sequence selected from SEQ ID NOs: 2-7.

In another preferred embodiment, the G-CSF dimer is prepared by following the steps of:
a). transforming mammalian cells with an expression vector comprising a DNA sequence encoding a G-CSF-Fc complex, wherein the DNA sequence is selected from SEQ ID NOs: 9-10;
b). culturing the mammalian cells under conditions sufficient for expressing the G-CSF-Fc complex and the G-CSF dimer; and
c). isolating and purifying the G-CSF dimer;
wherein the G-CSF dimer comprises two G-CSF-Fc complexes in which each G-CSF-Fc complex comprises an amino acid sequence selected from SEQ ID NOs: 2-7.

According to the present invention, the composition herein is a pharmaceutical composition, a nutraceutical composition, or a food composition.

The pharmaceutical composition is a solid or liquid formulation.

The pharmaceutical composition comprises 0.01-99 wt % G-CSF dimer and a pharmaceutically acceptable excipient or carrier.

The pharmaceutically acceptable excipient or carrier is selected from: cellulose and its derivatives, gelatin, speckstone, solid lubricating agent, calcium sulphate, plant oil, polyols, emulsifier, wetting agent, colorant, flavoring agent, stabilizer, anti-oxidant, antiseptic, and pyrogen-free water.

In another preferred embodiment, the medicine containing G-CSF dimer is used to increase the concentration of dopamine in corpus striatum; prevent the loss of dopaminergic nerve fiber; and/or prevent the loss of dopaminergic neuron.

In a second aspect of the present invention, a medicament for treating a neurodegenerative disease is provided, which comprises G-CSF dimer as an active ingredient.

The neurodegenerative disease is selected from: Parkinson's disease, Alzheimer's disease, Huntington disease, amyotrophic lateral sclerosis, spinal muscular atrophy, primary lateral sclerosis, and spinal cerebellar ataxias.

The G-CSF dimer is a human G-CSF dimer.

The pharmaceutical composition comprises 0.01-99 wt % human G-CSF dimer and residual pharmacologically acceptable excipients or carriers.

The structure of the G-CSF dimer herein is shown as formula I:

$$M1-L-M2 \qquad \qquad I$$

wherein M1 is a first monomer of human G-CSF; M2 is a second monomer of human G-CSF; and L is a linker connecting said first monomer and said second monomer and disposed therebetween.

Also, the G-CSF dimer retains the biological activity of G-CSF monomer and has a serum half-life of longer than twice of that of either the first or said second monomer.

In a third aspect of the present invention, a method of treating a neurodegenerative disease comprising administrating a G-CSF dimer to a subject in need of the treatment is provided.

The neurodegenerative disease is selected from: Parkinson's disease, Alzheimer's disease, Huntington disease, amyotrophic lateral sclerosis, spinal muscular atrophy, primary lateral sclerosis, and spinal cerebellar ataxias.

In another preferred embodiment, the subject comprises a mammal (such as a human).

The G-CSF dimer molecules of the present invention can significantly increase the concentration of dopamine in corpus striatum in PD animal model, inhibit the loss of dopaminergic nerve fiber, and increase the number of dopaminergic neurons in substantia nigra in PD animal model, and enhance the functions of dopaminergic neurons. In addition, the G-CSF dimer molecules can significantly improve learning and memory capacity of AD model rats, protect neurons, reduce neuronal apoptosis in hippocampus, and alleviate the syndromes of dementia. The G-CSF dimer of the present invention has a prolonged half-life in serum and is capable of effectively preventing neuronal loss, consequently enabling more effective treatment of neurodegenerative diseases.

It is clear for a skilled person in the art that, the technical features mentioned above and described in the examples below of the present invention could be combined with each other to result in a new or preferred technical solution. Hence this invention should not be construed as limited to the embodiments set forth herein.

BRIEF DESCRIPTION OF FIGURES

In FIG. 2a, the oval-shaped object labeled with "C" represents a carrier protein wherein the G-CSF monomer is disposed at the N-terminal of the carrier protein. FIG. 2b shows the pairing of two Fc via disulfide bond.

In FIG. 3a, the oval-shaped object labeled with "C" represents a carrier protein wherein the G-CSF monomer is disposed at the C-terminal of the carrier protein. FIG. 3b shows the pairing of two Fc via disulfide bond.

DETAILED DESCRIPTION OF THE PREFERRED EMBODIMENTS

Upon an extensive and thorough research, the inventors have created a G-CSF dimer for the first time and have surprisingly found that the G-CSF dimer of the present invention has a prolonged in vivo half-life, can improve pharmacokinetic properties of the drug, reduce the drug administration frequency, enhance in vivo bioactivity, reduce the symptoms of neurodegenerative diseases, and promote the recovery from neurodegenerative diseases. The present invention is achieved upon these surprising discoveries.

G-CSF Dimer

The structure of G-CSF dimer according to the present invention is shown as formula I:

$$M1-L-M2 \qquad \qquad I$$

wherein M1 is a first monomer of human G-CSF; M2 is a second monomer of human G-CSF; and L is a linker connecting said first monomer and said second monomer and disposed therebetween.

Also, the G-CSF dimer retains the biological activity of G-CSF and has a serum half-life of longer than twice of that of either the first or the second monomer.

The biological activity includes:
a) acting on neutrophil granulocyte precursor cells and bone marrow stem cells to drive the differentiation, growth, and maturation of neutrophils; and
b) activating mature neutrophils to participate in immune response.

In another exemplary embodiment, the first monomer and the second monomer are identical. The amino acid sequence of the first monomer and the second monomer is shown as SEQ ID NO: 8.

In another exemplary embodiment, the linker L is selected from the group consisting of:
(i) a short peptide comprising 3 to 50 amino acids; and
(ii) a polypeptide of formula II:

$$-Z-Y-Z- \qquad \qquad II$$

wherein Y is a carrier protein; Z is nothing, or a short peptide comprising 1 to 30 amino acids. "-" is a chemical bond or a covalent bond. Preferably "-" is a peptide bond.

Figure 1:
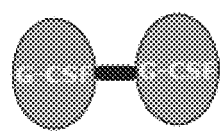
FIG. 1 is an illustration of the structure of a G-CSF dimer according to the present invention. In the figure, "-" represents a linker and the oval-shaped object labeled with "G-CSF" represents a G-CSF monomer.
Figure 2A:
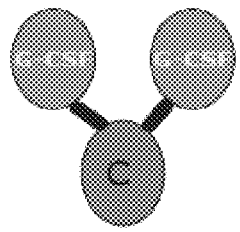
FIGS. 2a and 2b are illustrations of the structure of a G-CSF dimer according to the present invention. In the figures, "-" represents an amino acid linker and the oval-shaped object labeled with "G-CSF" represents a G-CSF monomer.
Figure 2B:
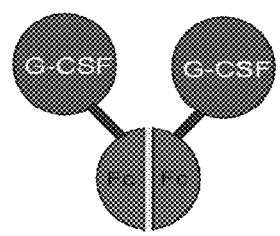
Figure 3A:
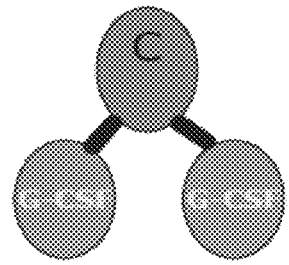
FIGS. 3a and 3b are illustrations of the structure of a G-CSF dimer according to the present invention. In the figures, "-" represents an amino acid linker and the oval-shaped object labeled with "G-CSF" represents a G-CSF monomer.
Figure 3B:
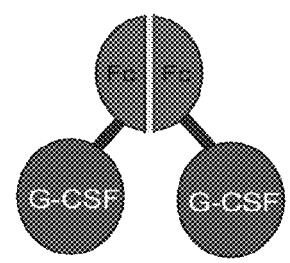

Representative structural illustrations of a G-CSF dimer are shown in FIGS. 1-3. The carrier protein comprises (but is not limited to) Fc fragment of human IgG1, IgG2, IgG3, or IgG4, or human albumin.

G-CSF can be disposed at the C-terminal or the N-terminal of the carrier protein.

As used herein, "linker" refers to an oligopeptide between one G-CSF monomer and another G-CSF monomer and connecting the two monomers together. There is no specific limitation on the length of the linker. A linker is usually 5-50 amino acid residues in length and in general, a linker does not affect or significantly affect the proper fold or conformation of the two G-CSF monomers. Some examples of linkers include (but are not limited to):

Preferably, the linker contains an amino acid sequence selected from:
(a) an amino acid sequence with 3-15 hydrophobic amino acid residues Gly or Pro, such as Gly-Pro-Gly-Pro-Gly-Pro (SEQ ID NO: 11); or an amino acid sequence with 3-20 amino acid residues Gly or Ser, such as GSGG (SEQ ID NO: 12).
(b) an amino acid sequence encoded by multiple cloning sites. Such sequences usually contain 5-20 amino acid residues, preferably 10-20 amino acid residues. Examples include (but are not limited to): TGLQPTRGIDDITSPVD (SEQ ID NO: 13);
(c) an amino acid sequence of a protein other than G-CSF monomer, such as an amino acid sequence of IgG or albumin;
(d) an amino acid sequence comprising any combination of (a), (b), and (c) above.

In one preferred embodiment, the linker has the sequence of GSGGGSGGGGSGGGGS (i.e. amino acid residues 175-190 of SEQ ID NO: 1).

In another exemplary embodiment, the linker has the sequence of ASTKGP (i.e. amino acid residues 175-180 of SEQ ID NO: 4).

In addition, an amino acid sequence not affecting the biological activity of G-CSF monomer can be added to the N-terminal or the C-terminal of the fusion protein. In a preferred embodiment, such appended amino acid sequence is beneficial to expression (e.g. signal peptide), purification (e.g. 6×His sequence, the cleavage site of *Saccharomyces cerevisiae* α-factor signal peptide), or enhancement of biological activity of the fusion protein.

Sequence Listing

SEQ ID NO: 1 represents a sequence of a G-CSF dimer as shown in FIG. 1 comprising a G-CSF monomer (amino acid residues 1-174) connected to another G-CSF monomer (amino acid residues 191-364) by a linker (amino acid residues 175-190).

SEQ ID NO: 2 represents a sequence of a G-CSF monomer with Fc fragment that forms part of a G-CSF dimer comprising a G-CSF monomer (amino acid residues 1-174), a Fc fragment of human IgG2 (amino acid residues 191-418), and a linker connecting said G-CSF monomer and said Fc fragment (amino acid residues 175-190). As shown in FIGS. 2a and 2b, two G-CSF monomers with Fc fragment form a dimer through the pairing of the two Fc fragments via a plurality of disulfide bonds disposed therebetween;

SEQ ID NO: 3 represents a sequence of a G-CSF monomer with Fc fragment that forms part of a G-CSF dimer comprising a G-CSF monomer (amino acid residues 245-418), a Fc fragment of human IgG2 (amino acid residues 1-228), and a linker connecting said G-CSF monomer and said Fc fragment (amino acid residues 229-244). The two G-CSF monomers with Fc fragment form a dimer through the pairing of the two Fc fragments via a plurality of disulfide bonds disposed therebetween;

SEQ ID NO: 4 represents a sequence of a G-CSF monomer with Fc fragment that forms part of a G-CSF dimer comprising a G-CSF monomer (amino acid residues 1-174), a Fc fragment of human IgG2 (amino acid residues 181-403), and a linker connecting said G-CSF monomer and said Fc fragment (amino acid residues 175-180). The two G-CSF monomers with Fc fragment form a dimer through the pairing of the two Fc fragments via a plurality of disulfide bonds disposed therebetween;

SEQ ID NO: 5 represents a sequence of a G-CSF monomer with Fc fragment that forms part of a G-CSF dimer comprising a G-CSF monomer (amino acid residues 230-403), a Fc fragment of human IgG2 (amino acid residues 1-223), and a linker connecting said G-CSF monomer and said Fc fragment (amino acid residues 224-229). The two G-CSF monomers with Fc fragment form a dimer through the pairing of the two Fc fragments via a plurality of disulfide bonds disposed therebetween;

SEQ ID NO: 6 represents a sequence of a G-CSF monomer with Fc fragment that forms part of a G-CSF dimer comprising a G-CSF monomer (amino acid residues 1-174), a Fc fragment of human IgG2 (amino acid residues 191-413), and a linker connecting said G-CSF monomer and said Fc fragment (amino acid residues 175-190). The two G-CSF monomers with Fc fragment form a dimer through the pairing of the two Fc fragments via a plurality of disulfide bonds disposed therebetween;

SEQ ID NO: 7 represents a sequence of a G-CSF monomer with Fc fragment that forms part of a G-CSF dimer comprising a G-CSF monomer (amino acid residues 240-413), a Fc fragment of human IgG2 (amino acid residues 1-223), and a linker connecting said G-CSF monomer and said Fc fragment (amino acid residues 224-239). The two G-CSF monomers with Fc fragment form a dimer through the pairing of the two Fc fragments via a plurality of disulfide bonds disposed therebetween;

SEQ ID NO: 9 represents the cDNA sequence of SEQ ID NO: 2.

SEQ ID NO: 10 represents the cDNA sequence of SEQ ID NO: 6.

Compared to the G-CSF monomer, at an equal molar concentration of G-CSF molecules (the concentration of G-CSF dimer is 0.1-1,000 ng/mL, preferably 1-100 ng/mL; the concentration of G-CSF monomer is 0.04-400 ng/mL, preferably 0.4-40 ng/mL), the G-CSF dimer of the present invention showed stronger protective effects on MPP+ induced PC12 cells, and stronger biological activity to activate STAT3 in dopaminergic neurons. The G-CSF dimer led to significant improvement on the MPTP-induced abnormal behavior of animal, significant increase of the concentration of dopamine in corpus striatum in MPTP-induced animal, and remarkable prevention of the mass loss of dopaminergic neuron induced by MPTP, showed significantly stronger biological activity to activate STAT3 in hippocampus neurons, and led to attenuation of the apoptosis of PC12 cells induced by Aβ, and improvement on the learning and memory ability in animal model of AD.

Preparation Method

DNA sequences encoding the G-CSF dimer or fusion protein of the present invention can be entirely artificially synthesized. Alternatively, the DNA sequences encoding the first G-CSF monomer and/or the second G-CSF monomer can be obtained by PCR amplification or synthesis and joined together to form the DNA sequence encoding the fusion protein of the present invention.

In order to enhance the expression volume of the host cells, modification can be performed on the sequence encoding the G-CSF dimer. For example, codons preferred by the host cells can be used to eliminate sequences that are not beneficial to transcription and translation. In an exemplary embodiment of the present invention, codons preferred by mammalian cells are used together with DNA software for assaying the gene of the G-CSF dimer, to eliminate sequences that are not beneficial to transcription and translation from the gene. The eliminated sequences can be intron cutting site, transcription terminating sequence, etc.

After the DNA sequence encoding the novel fusion protein of the present invention is obtained, it is first inserted into an appropriate expression carrier, followed by transformation into an appropriate host cell. Finally, the transformed host cells are cultivated and the novel fusion protein of the present invention is isolated and purified.

As used herein and in the claims, "carrier" refers to plasmid, cosmid, expression vector, cloning vector, and virus vector, etc.

In the present invention, carriers known in the art, such as carriers available in the market, can be used. For example, with the use of carrier obtained from the market, nucleotide sequence encoding the novel fusion protein of the present invention can be operationally connected to an expression control sequence to form the protein expression carrier.

As used herein, "operationally connected" refers to a scenario that some parts of a linear DNA sequence can affect the activity of other parts of the same linear DNA sequence. For instance, if signal peptide DNA is used for the expression of a precursor that participates in secretion of polypeptides, then said signal peptide (secretion leader sequence) DNA is "operationally connected" to the polypeptide DNA. If a promoter controls the transcription of a sequence, the promoter is "operationally connected" to the encoded sequence. If a ribosome binding site is situated at a position where translation thereof is made possible, said ribosome binding site is "operationally connected" to the encoded sequence. In general, "operationally connected" means that the residues of concern are in proximity; for secretion of the leader sequence, "operationally connected" refers to proximity within the reading frame.

As used herein, "host cells" refers to both prokaryotic cells and eukaryotic cells. Prokaryotic host cells commonly used include *E. coli, B. subtilis*, etc. Eukaryotic host cells commonly used include yeast cells, insect cells, mammalian cells, etc. In a preferred embodiment, the host cells used are eukaryotic cells; in a more preferred embodiment, the host cells used are mammalian cells.

After the transformed host cells are obtained, they can be cultivated under a condition suitable to express the fusion protein of the present invention for expressing the fusion protein. The expressed fusion protein is then separated.

According to one embodiment, a method for manufacture of a G-CSF dimer of the present invention comprises the steps of:

a) transforming mammalian cells with an expression vector comprising a DNA sequence encoding a G-CSF-Fc complex, wherein the DNA sequence is selected from SEQ ID NO: 9-10;
b) culturing the transformed mammalian cells under conditions sufficient for expressing the G-CSF-Fc complex and the G-CSF dimer; and
c) isolating and purifying the G-CSF dimer;
wherein the G-CSF dimer comprises two G-CSF-Fc complexes and the amino acid sequence of each G-CSF-Fc complex is selected from SEQ ID NOs: 2-7.

Pharmaceutical Composition and Method of Administration Thereof

Since the G-CSF dimer of the present invention has an excellent serum half-life, the G-CSF dimer of the present invention and a pharmaceutical composition comprising the G-CSF dimer of the present invention as the main active ingredient can be used for treating a disease associated with neural injury, and for protecting neurons. The disease is selected from a group consisting of: Parkinson's disease ("PD"), Alzheimer's disease ("AD"), Huntington disease ("HD"), amyotrophic lateral sclerosis ("ALS"), spinal muscular atrophy ("SMA"), primary lateral sclerosis ("PLS"), and spinal cerebellar ataxias ("SCA").

The diseases mentioned in the present invention include those diseases accompanied with neurodegenerative disorders. Although neurologic disease can be induced by various causes, and can appear in various locations or nerves, the restoration of the damaged nerve and the improvement of the nerve function induced by the medicine of the present invention indicate that the medicine is effective in treating and improving different types of neurodegenerative diseases. The diseases referred to in the present invention include, but are not limited to, Parkinson's disease ("PD"), Alzheimer's disease ("AD"), Huntington disease ("HD"), amyotrophic lateral sclerosis ("ALS"), spinal muscular atrophy ("SMA"), primary lateral sclerosis ("PLS"), and spinal cerebellar ataxias ("SCA"), spinocerebellar degeneration, cerebrosclerosis, striatonigral degeneration, Friedreich ataxia, amyloidosis, and subacute myelo-optico-neuropathy ("SMON"). Also included is a method of treating these diseases and/or a use in the manufacture of medicament for treating any one of the diseases described herein.

Via an appropriate route of administration, the medicine of the present invention can be administered into an appropriate position whose choice depends on the diseases and the symptoms to be treated. For instance, for the diseases mainly accompanied with degenerative disorders in brain, the medicine may be administered into brain; for the diseases accompanied with focal degenerative disorders in corpus striatum, the medicine may be administered into corpus striatum; for the diseases accompanied with systemic neurodegenerative disorders, the medicine may be administered systematically. Preferred route of administration is an appropriate method such as injection. Preferred route of administration of the medicine of the present invention comprises administration of the medicine to the locations where neurodegeneration occurs, arterial administration, intravenous administration and subcutaneous administration.

The pharmaceutical composition of the present invention comprises a safe and effective amount of said G-CSF dimer and a pharmaceutically acceptable excipient or carrier. "Safe and effective amount" refers to an amount of a compound sufficient to substantially improve the condition of the patient in need thereof without causing serious side-effects. The safe and effective amount is determined based on the specific circumstances such as age, condition, and regimen associated with a subject of treatment. In general, the pharmaceutical composition comprises 1-1,000 mg of G-CSF dimer per dose; in a preferred embodiment, the pharmaceutical composition comprises 0.05-300 mg of G-CSF dimer per dose; in a more preferred embodiment, the pharmaceutical composition comprises 0.3-200 mg of G-CSF dimer per dose.

"Pharmaceutically acceptable excipient or carrier" refers to one or more compatible solid or liquid filling or gelatin materials which are suitable to be used in human with sufficient purity and sufficiently low toxicity. "Compatibility" refers to the ability of each ingredient of the composition to mutually blend with the compound of the present invention and the mutual blending ability between the ingredients, without substantially decreasing the clinical efficacy of the compound. Some of the examples of pharmaceutically acceptable excipient or carrier include cellulose and its derivatives (e.g. sodium carboxymethylcellulose, sodium ethylcellulose, cellulose acetate, etc), gelatin, speckstone, solid lubricating agent (e.g. stearic acid, magnesium stearate), calcium sulphate, plant oil (e.g. pea oil, sesame oil, peanut oil, olive oil, etc.), polyols (e.g. propylene glycol, glycerol, mannitol, sorbitol, etc.), emulsifier (e.g. Tween®), wetting agent (e.g sodium lauryl sulfate), colorant, flavoring agent, stabilizer, anti-oxidant, antiseptic, pyrogen-free water, etc.

Route of administration of the G-CSF dimer of the present invention comprises oral administration, rectal administration, parenteral administration (intravenous, intramuscular, or subcutaneous), and partial administration. Solid form for oral administration comprises capsules, tablets, pills, powder, and granules. In these solid forms, active compound is mixed with at least one of the conventionally inert excipients (or carriers), such as sodium citrate, dicalcium phosphate, or any of the following ingredients: (a) filing or bulking agent, e.g. starch, lactose, sucrose, glucose, mannitol, and silicic acid; (b) adhesion agent, e.g. carboxymethylcellulose, alginate, gelatin, polyvinyl pyrrolidone, sucrose, and acacia; (c) humectants, e.g. glycerol; (d) disintegrating agent, e.g. agar, calcium carbonate, potato starch or cassava starch, alginic acid, compounded silicate, and sodium carbonate; (e) buffering agent, e.g. paraffin wax; (f) absorption accelerating agent, e.g. quaternary amine compound; (g) wetting agent, e.g. cetanol and glycerin monostearate; (h) absorbent, e.g. bolus alba; and (i). lubricating agent, e.g. speckstone, calcium stearate, magnesium stearate, solid polyethylene glycol, sodium lauryl sulfate, or any mixture thereof. Capsules, tablets, and pills can also comprise buffering agent. Solid forms such as tablets, sugar pill, capsules, pills, and granules can be prepared with coating and core-shell materials, such as casing and other materials known in the art. These materials can comprise opacifying agent and the active compound or compound in such composition can be released in a delayed fashion that the release is done in certain part of the alimentary canal. Embedding component such as polymer materials and wax materials can be used. If desired, active compounds can be mixed with one or more of the above-described excipients to formulate a micro capsule form.

Liquid forms for oral administration comprise pharmaceutically acceptable emulsion, solution, suspension, syrup, or tincture. Apart from active compounds, liquid forms can also comprise inert diluents conventionally used in the art such as water or other solvent, solubilizing agent and emulsifier such as ethanol, isopropanol, carbonate acetate, ethyl acetate, propan-2-ol, 1,3-butan-2-ol, dimethylfomamide, and oil, in particular cotton oil, peanut oil, maize embryo oil, olive oil, castor oil, and sesame oil or any mixture thereof.

Apart from these inert diluents, the composition can also comprise additives, such as wetting agent, emulsifying agent, suspending agent, sweetening agent, correctives, and spices.

Apart from active compounds, suspension can also comprise suspending agent, such as ethoxyl isostearic alcohol, polyoxyethylene sorbitol, sorbitan, microcrystalline cellulose, aluminium methoxide, agar, or any mixture thereof.

Compositions used for parenteral administration can also comprise physiologically acceptable sterile water or anhydrous solution, dispersion solution, suspension, or emulsion, and sterile powder that can be re-dissolved into sterile injectable solution or dispersion solution. Appropriate hydrated or anhydrous carriers, diluting agent, solvent, or excipient comprise water, ethanol, polyols, and appropriate mixtures thereof.

Forms of the G-CSF dimer of the present invention used for partial administration comprise ointment, powder, patch, sprayer, and inhalant. Under sterile conditions, active components can be mixed with physiologically acceptable carrier and any antiseptic, buffering agent, or propellant if desired.

The G-CSF dimer of the present invention can be solely administered or be administered in conjunction with any pharmaceutically acceptable compounds.

On using the pharmaceutical composition, a safe and effective amount of the G-CSF dimer of the present invention is administered to a mammal (e.g. a human) in need thereof, wherein the dosage administered is a pharmaceutically effective administration dosage. For a human of 60 kg, the administration dosage is usually 0.01-300 mg; in a preferred embodiment, the administration dosage is 0.5-100 mg. In determination of the actual dosage, factors known in the art such as administration route and patients' health condition, etc. have to be considered, of course, which are within the skills of a skilled physician in the art.

The main advantages of the present invention include:

A longer in vivo biological half-life.

Significantly increasing the concentration of dopamine in corpus striatum in animal model of PD, inhibiting the loss of dopaminergic nerve fibers in corpus striatum and dopaminergic neurons in substantia nigra in animal model of PD, and enhancing the function of dopaminergic neurons.

Significantly decreasing the apoptosis of neurons in hippocampus and improving learning and memory capacity of animal model of AD.

Remarkable neuro-protective effect in neurodegenerative diseases and enabling therapeutic efficacy in the treatment of neurodegenerative diseases.

The following exemplary embodiments further describe the present invention. Although the description referred to particular embodiments, it will be clear to one skilled in the art that the present invention may be practiced with variation of these specific details. Hence this invention should not be construed as limited to the embodiments set forth herein. Further, for the embodiments in which details of the experimental methods are not described, such methods are carried out according to conventional conditions such as those described in Sambrook et al. Molecular Cloning: A Laboratory Manual (New York: Cold Spring Harbor Laboratory Press, 1989), or as suggested by the manufacturers.

Example 1

Preparation of G-CSF Dimer

The G-CSF dimer of the present invention has an amino acid sequence of SEQ ID NO: 1 or comprises dimers as illustrated in FIGS. 1-3 comprising G CSF-Fc complexes with an amino acid sequence selected from SEQ ID NOs: 2-7. Preparation methods are described as follows:

a. Construction of a Cell Line Expressing G-CSF Dimer

The full length cDNA sequence of the G-CSF-Fc complexes (such as the sequence shown in SEQ ID NO: 10 or SEQ ID NO: 9) was synthesized. cDNA sequence of human G-CSF monomer was connected with cDNA sequence of Fc fragment of IgG2. cDNA sequences containing HindIII site, and expression elements required by mammalian cell such as Kozak sequence and signal peptide sequence were introduced at the 5' end. cDNA sequence containing EcoRI site was introduced at the 3' end. The full length cDNA sequence was cloned into pUC19 plasmid to obtain pG-CSF-Fc, which was used to transform *E. coli* TG1. The plasmid was digested with HindIII and EcoRI, and an approximately 1400 bp G-CSF-IgG2Fc fragment was harvested and connected with pcDNA3 (Invitrogen) expression plasmid which was also digested with HindIII and EcoRI, and an expression plasmid pEX-G-CSF-Fc was then constructed. Expression plasmid pEX-G-CSF-Fc was linearized, purified and transfected into CHO cells by electroporation. The transfected cells were selected in selecting media. The expression levels of individual clones were measured by ELISA. The cell lines with the higher protein expression levels were selected and cells thereof were frozen to generate a cell bank.

According to the steps as above described, expression vectors comprising cDNA sequence encoding each of SEQ ID NOs: 2-7 can be constructed, then linearized and transfected into CHO cells to express G-CSF dimer. The expression levels can be measured by ELISA and cell lines with higher G-CSF-Fc dimer expression levels can be selected to generate a cell bank.

b. Large-Scale Cell Culture

One vial of cells (~1×107 cells/mL) from the cell bank was thawed and seeded in 10 mL basal medium in a 10 cm Petri dish and incubated at 37° C., 5% $CO_2$ for 24 hr.

The seeding expansion: the 10 mL culture was sequentially expanded in volumes of 30-40 mL. When the cell density reached 1.0–1.5×106 cells/mL with viability ≥90%, the culture volume was expanded to 300-400 mL step by step. The shaking flasks were incubated at 120 rpm 37° C., 5% $CO_2$.

Culture expansion in a bioreactor (3 L-10 L): when the cell density in the seeding expansion reached 1.0–3.0×106 cells/mL with viability ≥90%, 300-400 mL of the seeding expansion culture was aseptically transferred to a 3-10 L bioreactor with the culture conditions controlled at pH of 6.8, dissolved oxygen at approximately 50% and stirring speed at 65-100 rpm.

Culture production in a bioreactor (30-100 L): when the cell density in the 3-10 L bioreactor reached 1.0–3.0×10$^6$ cells/mL with viability ≥90%, the culture was aseptically transferred to a 30-100 L bioreactor with the culture conditions controlled at pH of 6.8, dissolved oxygen at approximately 50% and stirring speed at 65-100 rpm. The culture was fed at 12 to 48 hr to control the glucose level in the medium (<1 g/L) via a fed-batch culture.

c. Separation and Purification of G-CSF Dimer

After the culture expansion in bioreactor, cell supernatant was harvested which contained G-CSF-Fc complex, G-CSF dimer, G-CSF-Fc multi-mers, and metabolites. After being harvested from the bioreactor culture, the cell culture supernatant was obtained by filtration and purified by a series of gel chromatography methods; for example, captured using a rProtein A Sepharose FF (GE Healthcare, cat#17-1279-04), eluted with a buffer containing 50 mM critic acid/sodium citrate and 0.2M NaCl at pH 3.7-3.8, resulting in >90% pure G-CSF dimer. Additional chromatography steps were performed using Capto Adhere column with elution buffer of 50 mM NaAc/HAC and 0.2 M NaCl at pH 4.5-5.0, followed by SP Sepharose FF (GE Heathcare Cat #17-0729-04) and balanced with equilibrium buffer of 10 mM PB (pH 6.0±0.1). Elution buffer used was 10 mM PB and 0.2M NaCl (pH 7.2±0.1). Additional processes involved viral inactivation at low pH, filtration, etc., resulting in G-CSF dimer.

The purity of the isolated and purified G-CSF dimer was >95% (analyzed by reverse phase HPLC), with estimated molecular weight of 47±5 kD (analyzed by reduced SDS-PAGE analysis). The G-CSF dimer was O-glycosylated with oligosaccharide of 2-10% of the total molecular weight. The isoelectric point of the protein was 5.8-6.8. The maximum UV absorbing wavelength was at 280 nM. The G-CSF dimer can activate STAT3 in M-NSF-60 cells and stimulate the proliferation of M-NSF-60 cells in vitro (the ED50 thereof was 0.1-10 ng/mL).

Example 2

In Vivo Half-Life of G-CSF Dimer

Rats received a single dose of 100 μg/kg of G-CSF dimer consisting of two G-CSF-Fc complexes (SEQ ID NO: 3) by subcutaneous injection. The pharmacokinetic parameters were calculated and listed in Table 1 below (n=6). The half-life of G-CSF monomer in rats was approximately 2 hr.

TABLE 1

Pharmacokinetic Parameters

| Parameter (n = 6) | Unit | Average Value | SD |
|---|---|---|---|
| $AUC_{(0-t)}$ | ng/mL * h | 4234.8 | 640.3 |
| $MRT_{(0-t)}$ | h | 21.6 | 1.4 |
| $t_{(1/2)}$ | h | 7.7 | 1.2 |
| Clz/F | L/h/kg | 0.024 | 0.003 |
| $C_{max}$ | ng/mL | 162.2 | 30.2 |

Example 3

Pharmacokinetic Properties of G-CSF Dimer in Human Beings 24 healthy subjects were randomly divided into four dosage groups of 30, 60, 120, 240 μg/kg respectively receiving a single dose of 30, 60, 120, 240 μg/kg of G-CSF dimer (comprising two G-CSF-Fc monomers with sequence shown in SEQ ID NO: 6). Blood samples were collected at the 0.5, 1st, 2nd 4th, 8th, 16th 24th, 36th, 48th, 72nd, 96th hour, Day 6 (120 hours), 7, 9, 11, 13, and 15 after administration. Serum was separated and stored in −70° C. freezer. The blood drug concentrations were measured by ELISA (ELISA, Quantikine human G-CSF ELISA kit, R&D System, Inc. Minneapolis, Min, Cat: PDCS50). The pharmacokinetic parameters were calculated using the non-compartmental analytical procedures (Software WinNonlin v 5.2, Pharsight Corporation, USA). The results were shown in Table 2.

TABLE 2

Pharmacokinetic Parameters

| Parameter (n = 6) | 30 μg/kg | 60 μg/kg | 120 μg/kg | 240 μg/kg |
|---|---|---|---|---|
| $C_{max}$ (ng/mL) | 21.3 (10.3) | 44.6 (17.7) | 219.9 (76.6) | 759 (160) |
| $T_{max}$ (h, median & range) | 8 (8-16) | 8 (8-16) | 16 (16-36) | 36 (36) |
| $t_{1/2}$ (h) | 43.9 (4.3) | 56.1 (23.3) | 59.3 (23.5) | 62.8 (10.8) |
| $AUC_{(0-inf)}$ (ng · h/mL) | 778 (213) | 1847 (686) | 8349 (2769) | 46664 (17258) |
| CL/F (mL/h/kg) | 41.4 (12.8) | 36.8 (14.6) | 18.5 (7.7) | 5.7 (2.0) |

Additionally, G-CSF dimer was shown to exhibit good safety and tolerance in this clinical trial.

Example 4

Protective Effect on PC12 Cells from MPP+ Induced Neurotoxicity

PC12 cell is a cell line derived from a pheochromocytoma of rats. The ability of PC12 in synthesis, metabolism, and delivery of dopamine has been shown in culture in vitro. PC12 cell line can be used as an in vitro model for screening active compounds.

PC12 cells were experimentally seeded at a density of 40,000 per well in 96-well plates in the following medium: DMEM, 10% horse serum +5% FCS, 1% Penicillin-Streptomycin. MPP+(Sigma) was added to final concentrations of 30-3,000 μm. G-CSF was added to yield final concentrations of 0.4 ng/mL, 4 ng/mL, and 40 ng/mL, respectively. G-CSF dimer was added to yield final concentrations of 1 ng/mL, 10 ng/mL, and 100 ng/mL respectively. After 24 hr of culture, cell viability was determined by a fluorimetric cell viability assay. The results showed that the survival rate of PC12 cells decreases with increasing MPP+ concentrations upon MPP+ treatment, and that under an identical MPP+ concentration, the protective effect of G-CSF dimer on the PC12 cell survival is significantly higher, compared with G-CSF monomer at an equal molar concentration of G-CSF molecule.

PC12 cells were seeded at a density of 40,000 in 96-well plates in the following medium: DMEM, 10% horse serum +5% FCS, 1% Penicillin-Streptomycin. MPP+(Sigma) was added to final concentrations of 30-3,000 μm. G-CSF monomer was added to yield final concentrations of 0.4 ng/mL, 4 ng/mL, and 40 ng/mL, respectively. G-CSF dimer was added to yield final concentrations of 1 ng/mL, 10 ng/mL, and 100 ng/mL, respectively. After 24 hr of culture, the level of tyrosine hydroxylase (TH) was assayed by immunohistochemistry, and the number of TH-positive cells in substantia nigra was counted. The results demonstrated that the TH-positive cell number of G-CSF dimer-treated group is significantly higher than that of G-CSF-treated group, and that the protective effect of G-CSF dimer on the PC12 cells is significantly better, compared with G-CSF monomer at an equal molar concentration of G-CSF molecule.

The ratio of the molecular weight of G-CSF monomer to that of G-CSF dimer (consisting of G-CSF-Fc complexes comprising a sequence selected from SEQ ID NOs: 2-7) is about 1:5. One mole of G-CSF dimer contains two moles of G-CSF monomer. Therefore, at an equal mole of G-CSF molecule, the mass ratio of G-CSF monomer to G-CSF dimer is about 1:2.5, namely the molar concentration of G-CSF molecule contained in 0.4 ng/mL G-CSF monomer is the same molar concentration as that of 1 ng/mL G-CSF dimer; the molar concentration of G-CSF molecule contained in 4 ng/mL G-CSF monomer is the same molar concentration as that of 10 ng/mL G-CSF dimer; the molar concentration of G-CSF molecule contained in 40 ng/mL G-CSF monomer is the same molar concentration as that of 100 ng/mL G-CSF dimer.

Example 5

Activation of STAT3 in Dopaminergic Neurons

Fetal rat brain was harvested from female SD rats at the 14th day of gestation, and then placed in prechilled D-Hanks solution. Substantia nigra was removed under dissection microscope and cut into small pieces of approximately 1 mm3. The minced substantia nigra was digested in 10 mL of 0.125% of trypsin, at 37° C. for 15 min. The tissue was aspirated and transferred into centrifuge tubes containing DMEM containing 10% FBS, pipetted for a few times with a pipettor. The supernatant was obtained and aspirated into another centrifuge tube after standing. Such steps were repeated for 2-3 times. The cells were cultured in serum-free neuron basal medium (Invitrogen, Cat 21103049) with serum-free additive of B27 (Invitrogen, Cat 17504044) for 8 days. The medium was replaced once every two days.

After 8 days of culture, the neurons were treated with various concentrations of G-CSF dimer (G-CSF-D) (the final concentrations of G-CSF dimer were 1, 10, and 100 ng/mL) or G-CSF monomer (the final concentrations of G-CSF were 0.4, 4, and 40 ng/mL) for 15 min, respectively (Schneider A et al. J Clin Invest 2005, 115(8):2083-2098). After completely removing the medium, the cells were washed twice with PBS and lysed with cell lysis buffer (Cell Signaling Technology, Cat: 9803; main ingredients containing 20 mM Tris-HCl (pH 7.5), 150 mM NaCl, 1 mM $Na_2EDTA$, 1 mM EGTA, 1% Triton, 2.5 mM sodium pyrophosphate, 1 mM beta-glycerophosphate, 1 mM $Na_3VO_4$, 1 μg/mL leupeptin, and 1 mM PMSF) according to the instruction thereof. The cells were lysed on ice for 20 min and scratched using cell scraper. Cell lysate was harvested and centrifuged at 12,000 rpm, 4° C. for 10 min. The supernatant was collected and protein concentration was determined. Additionally, the change in STAT3 phosphorylation level was measured in 100 μL of the supernatant using a STAT3 [pY705] ELISA kit (Invitrogen, Cat: KH00481).

At an equal molar concentration of G-CSF molecule, G-CSF dimer (G-CSF-D) has better biological activity of STAT3 activation in dopaminergic neurons than that of G-CSF monomer.

Example 6

Therapeutic Effect of an Animal Model of MPTP-Induced PD 1-methyl-4-phenyl-1,2,3,6-tetrahydropyridine(MPTP) can induce the massive loss of the dopaminergic neurons in sustantia nigra by specifically injuring dopaminergic neurons, thereby resulting in syndromes similar to Parkinson's disease.

Male C57/BL6J mice of 12-14 weeks old, weighing 20-22 g were used in this study. The animals were raised at a 24±2° C. room temperature, and kept under a 12 hr light/dark cycle with free access to food and water.

50 mice were randomly assigned to 5 groups with 10 mice in each group respectively: a solvent control group; a MPTP model group; a MPTP+G-CSF 40 μg/kg group; a MPTP+GCSF-D 40 μg/kg group; and a MPTP+GCSF-D 100 μg/kg group. The G-CSF-D was composed of two G-CSF-Fc complexes comprising a sequence selected from SEQ ID NOs: 2-7.

The mice were administered via intraperitoneal injection of MPTP (30 mg/kg) for 5 consecutive days. After one day of recovery (from day 7), mice in the MPTP+G-CSF 40 μg/kg group were daily administered with G-CSF s.c. at a dose of 40 μg/kg for 5 consecutive days; mice in MPTP+GCSF-D 40 μg/kg group received G-CSF-D s.c. at a dose of 40 μg/kg once on day 7 and day 9, respectively; mice in MPTP+GCSF-D 100 μg/kg group received G-CSF-D s.c. at a dose of 100 μg/kg once on day 7 and day 9, respectively; mice in solvent control group received equal volume of saline.

The animals were evaluated on the 12th day as follows:
Behavioral Tests on Mice of PD The behavior performance was tested on the 10th day following the last injection of MPTP. The method was pole test which has been used to assess slow movement of the animals, a typical behavior in PD. (Matsuura et al., 1997; Araki et al., 2001; Kato et al., 2004)

Mice were carefully placed on the top of a rough pole (8 mm in diameter and 55 cm in height) with their heads facing upwards. The time required for a mouse to turn head from upwards to downwards completely was recorded as T-turn (time to turn). The time for a mouse to climb to the bottom of pole until their four legs arrive the ground was recorded as T-LA (locomotion activity time). Time exceeding 30 sec was recorded as 30 sec. The test was repeated 5 times and its average value was used for each mouse.

The results show that G-CSF dimer significantly improved the behavior performance in MPTP-induced mice. Moreover, G-CSF dimer exhibited better efficacy than that of G-CSF monomer at equal molar concentration of G-CSF.

b. Determination of the Concentration of Dopamine in Corpus Striatum

Methods: After mice were sacrificed by decapitation, the striatum tissues were removed and kept in 1.5 mL centrifuge tube after weighing, then immediately put in ice. 300 μL sample processing solution (0.02M perchloric acid, 0.2 mM sodium pyrosulfite, 0.01% EDTA-2Na, containing 0.3 μM DHBA as an internal standard) was added to each 10 mg of sample in ice water bath. The above mixtures were homogenized by ultrasonic apparatus and then centrifuged at 10,000 g for 20 min under 4° C. The supernatants were removed and filtered through a 0.22 μM hydrophilic filter membrane. The concentrations of striatal dopamine were quantified using high performance liquid chromatography.

The results show that G-CSF dimer significantly increased the concentration of striatal dopamine in MPTP-induced mice. Moreover, G-CSF dimer exhibited better effecacy compared to G-CSF and had significant difference.

c. Observation of Dopaminergic Neurons in Substantia Nigra

Methods: Mice were anesthetized with 10% chloral hydrate. After perfusion with 4% paraformaldehyde, brains were removed and fixed with 4% paraformaldehyde for 24 hours. The samples were transferred in 10%, 20%, 30% sucrose solutions gradient dehydration until sinking to the bottom. The midbrains and striatums were coronally sectioned into slices with thickness of 20 µm at −20° C. by freezing microtome. TH is a specific marker for dopaminergic neurons. The slices of striatum and midbrain were incubated with the primary antibody which was a mouse monoclonal anti-TH antibody (1:1,000, CHEMICON) overnight at 4° C. After rinses in PBS for three times, the slices were incubated with biotin-conjugated secondary antibody at room temperature for 1 hr. SABC complexes were incubated at room temperature for 1 hr, followed by DAB staining, gradient dehydration in ethanol, transparency in xylene and the slides were sealed with neutral balsam. The optical density of TH-positive staining in the striatums was scanned and the number of TH-positive cells in the substantia nigra was counted.

The results showed that G-CSF dimer significantly protected from the massive loss of dopaminergic neurons induced by MPTP. Moreover, G-CSF dimer exhibited better efficacy compared to G-CSF and had significant difference.

Example 7

Activation of STAT3 in Hippocampal Neuron by G-CSF Dimer

Fetal rat brain was harvested from female SD rats at the 17th day of gestation, and then placed in prechilled D-Hanks solution. Hippocampus was carefully removed under dissection microscope and cut into small pieces of approximately 1 mm3. The minced substantia nigra was digested in 10 mL of 0.125% of trypsin, at 37° C. for 15 min. The supernatant was transferred into pre-chilled centrifuge tubes containing DMEM containing 10% FBS to stop the trypsin digestion and pipetted for a few times using a pipettor. After standing, the resulting supernatant was transferred to another centrifuge tube. Such steps were repeated for 2-3 times. The cells were cultured in serum-free neuron basal medium (Invitrogen, Cat: 21103049) with serum-free additive of B27 (Invitrogen, Cat: 17504044) for 8 days. The medium was replaced once every two days.

After 8 days of culture, the neurons were treated respectively with various concentrations of G-CSF dimer (consisting of two G-CSF-Fc complexes comprising a sequence selected from SEQ ID NOs: 2-7) (the final concentrations were 1, 10, and 100 ng/mL) or G-CSF (the final concentrations were 0.4, 4, 40 ng/mL) for 15 min, respectively (Schneider A et al. J Clin Invest 2005, 115(8):2083-2098). After completely removing the medium, the cells were washed twice with PBS and lysed with cell lysis buffer (Cell Signaling Technology, Cat.: 9803, containing 20 mM Tris-HCl (pH 7.5), 150 mM NaCl, 1 mM Na$_2$EDTA, 1 mM EGTA, 1% Triton, 2.5 mM sodium pyrophosphate, 1 mM beta-glycerophosphate, 1 mM Na3VO4, 1 µg/mL leupeptin, and 1 mM PMSF) according to the instruction thereof. The cells were lysed on ice for 20 min and scratched using cell scraper. Cell lysate was harvested and centrifuged at 12,000 rpm, 4° C. for 10 min. The supernatant was collected and protein concentration was determined. Additionally, the change in STAT3 phosphorylation level was measured in 100 µL of the supernatant using a STAT3 [pY705] ELISA kit (Invitrogen, Cat: KH00481).

At an equal molar concentration of G-CSF molecule, G-CSF dimer (G-CSF-D) has better biological activity of STAT3 activation in hippocampal neuron than that of G-CSF monomer.

Example 8

Protective Effect of G-CSF Dimer on Aβ-Induced Apoptosis of PC12 Cells

The neurite outgrowth of PC12 cells induced by the nerve growth factor (NGF) indicates that PC12 cells have characteristics of neurons. Amyloid β (Aβ)-induced apoptosis of PC12 cell line can be used as an in vitro AD model.

PC12 cells were cultured in basic culture medium (DMEM, 10% FCS, 1% Penicillin-Streptomycin), digested with trypsin, and resuspended in medium containing 50 ng/mL of NGF. PC12 cells were seeded at a density of 2×104 per well in 96-well plates and cultured at 37° C., 5% CO2 in an incubator for 24 hr. Aβ was added to yield final concentrations of 1-100 µm/L. The cells were incubated with G-CSF monomer at final concentrations of 0.4, 4, and 40 ng/mL receptively, or G-CSF-D (G-CSF dimers consisting of G-CSF-Fc complexes comprising a sequence selected from SEQ ID NOs: 2-7) at final concentrations of 1, 10, and 100 ng/mL receptively. Equal volume of PBS was added to the model wells and no Aβ was added to the negative control wells. After incubation for another 24 hr, cell morphology was determined by Hochest staining and cell proliferation was determined by MTT assay.

Compared to the negative control wells, the result of fluorescent nuclear staining of PC12 cells in the model wells was found to be obviously heterogeneous, showing solid and thick staining of hyperfluorescence of nucleus resulting from cell apoptosis, and that of G-CSF monomer treated group or G-CSF-D-treated cells was found to be well-distributed without solid and thick staining of distinct hyperfluorescence of nucleus. The results indicated that G-CSF dimer was able to inhibit the apoptosis of PC12 cells induced by Aβ upon differentiation stimulated by NGF, thus protecting the nerve cells.

Example 9

Therapeutic Effect of G-CSF Dimer on Aβ-Induced Animal Model of AD

Male SD mice with a body weight of 180-220 g were used. The animals were raised at a 24±2° C. room temperature, and kept under a 12 hr light/dark cycle with free access to food and water.

50 mice were randomly assigned to 5 groups with 10 mice in each group: a solvent control group; a Aβ model group; a group that received Aβ and G-CSF (40 µg/kg); a group that received Aβ and G-CSF-D (40 µg/kg); a group that received Aβ and G-CSF-D (100 µg/kg), wherein G-CSF-D consists of G-CSF-Fc complexes comprising a sequence selected from SEQ ID NOs: 2-7).

Experimental mice were anesthetized with 40 mg/kg sodium pentobarbital. The head was fixed and skin was disinfected. Upon a middle incision of the calvarium with 2 cm and dissection of the periosteum, the cranium was exposed. The skull of the mice was opened with a dental drill, and then mice were subjected to surgery at the following coordinates: 3.0 mm posterior to the bregma, 2.2 mm bilateral to the midline, and 2.8 mm ventral to the skull surface via microsyringe. The model group and drug-treated groups received an injection of 5 μl of Aβ1-40 solution (β amyloid protein) (2 μg/μL) respectively, while the sham-surgery group received an injection of 5 μL of saline.

3 days after modeling, mice in the Aβ+G-CSF (40 μg/kg) group were administered subcutaneously with G-CSF at a dose of 40 μg/kg once daily for 5 consecutive days. Mice in Aβ+GCSF-D 40 μg/kg group were administered subcutaneously with G-CSF-D at a dose of 40 μg/kg on day 3 and day 5 respectively. Mice in Aβ+GCSF-D 100 μg/kg group were administered subcutaneously with G-CSF-D at a dose of 100 μg/kg on day 3 and day 5 respectively. Mice in solvent control groups received equal volumes of saline.

The behavioral performance of mice was tested via the Morris water maze test on day 10.

After the behavioural test, mice were anesthetized with 10% chloral hydrate. After perfusion with 4% paraformaldehyde, brains were removed and fixed with 4% paraformaldehyde for 24 hours. The samples were transferred in 10%, 20%, 30% sucrose solutions gradient dehydration until sinking to the bottom. The hippocampuses were coronally sectioned into slices with thickness of 20 μm by freezing microtome at −20° C. NeuN (a neuronal nuclear antigen) is a specific marker for neurons. The slices of hippocampus were incubated with a primary antibody overnight at 4° C. After rinses in PBS for three times, the slices were incubated with biotin-conjugated secondary antibody at room temperature for 1 hr. SABC complexes were incubated at room temperature for 1 hr, followed by DAB staining, gradient dehydration in ethanol, transparency in xylene and the slides were sealed with neutral balsam. The number of NeuN-positive cells in the hippocampuses was counted.

The behavioral test showed that administration of G-CSF or G-CSF dimer significantly restored the functions of learning and memory in mice. Compared to the sham-surgery group, the number of NeuN-positive neurons decreased in the hippocampus of mice in model group. Compared to the model group, the numbers of NeuN-positive neurons in the hippocampus of mice in both the G-CSF and the G-CSF dimer-treated groups increased. Compared to the G-CSF monomer treated group, it was shown that the number of NeuN-positive neurons in the hippocampus of mice in G-CSF dimer-treated group (100 μg/kg) significantly increased.

Example 10

Therapeutic Effect of G-CSF Dimer on MPTP-Induced Animal Model of PD 1-methyl-4-phenyl-1,2,3,6-tetrahydropyridine (MPTP) can induce the massive loss of the dopaminergic neurons in sustantia nigra by specifically injuring dopaminergic neurons, resulting in syndromes similar to Parkinson's disease. Tyrosin hydroxylase (TH) which is a specific marker for dopaminergic neurons, can be used to quantitatively detect the number of dopaminergic neurons in substantia nigra.

Male C57/BL6J mice of 12-14 weeks old, weighing 22-30 g were randomly divided into 4 groups:

MPTP+G-CSF-D 30 μg/kg group: The animals received daily injection of MPTP at 30 mg/kg intraperitoneally for 5 consecutive days and allowed one day for recovery followed by subcutaneous administration of G-CSF-D at a dose of 30 μg/kg once on Days 7, 9, and 11 respectively.

MPTP+G-CSF-D 100 μg/kg group: The animals received daily injection of MPTP at 30 mg/kg intraperitoneally for 5 consecutive days and allowed one day for recovery followed by subcutaneous administration of G-CSF-D at a dose of 100 μg/kg once on Days 7, 9, 11 respectively.

MPTP model group: The animals received daily injection of MPTP at 30 mg/kg intraperitoneally for 5 consecutive days and allowed one day for recovery followed by administration of equal volumes of solvent (0.5% rat serum/PBS) from Day 7.

Normal control group: The animals received daily injection of equal volumes of saline for 5 consecutive days and allowed one day for recovery followed by administration of equal volumes of solvent (0.5% rat serum/PBS) from Day 7.

The aforesaid G-CSF dimer (G-CSF-D) consisted of two G-CSF-Fc with the sequence represented by SEQ ID NO: 6.

The animals were sacrificed on Day 12. The concentration of striatal dopamine was measured and assessment of the condition of dopaminergic nerve fibers and dopaminergic neurons in substantia nigra were performed.

a. Measurement of the Concentration of Dopamine in Striatum.

Methods: After mice were sacrificed by decapitation, the striatum tissues were removed and kept in 1.5 mL centrifuge tube after weighing, then immediately put in ice. 300 μL sample processing solution (0.02M perchloric acid, 0.2 mM sodium pyrosulfite, 0.01% EDTA-2Na, containing 0.3 μM DHBA as an internal standard) was added to each 10 mg of sample in ice water bath. The above mixtures were homogenized by ultrasonic apparatus and then centrifuged at 10,000 g for 20 min under 4° C. The supernatants were removed and filtered through a 0.22 μM hydrophilic filter membrane. The concentrations of striatal dopamine were quantified using high performance liquid chromatography.

Figure 4:
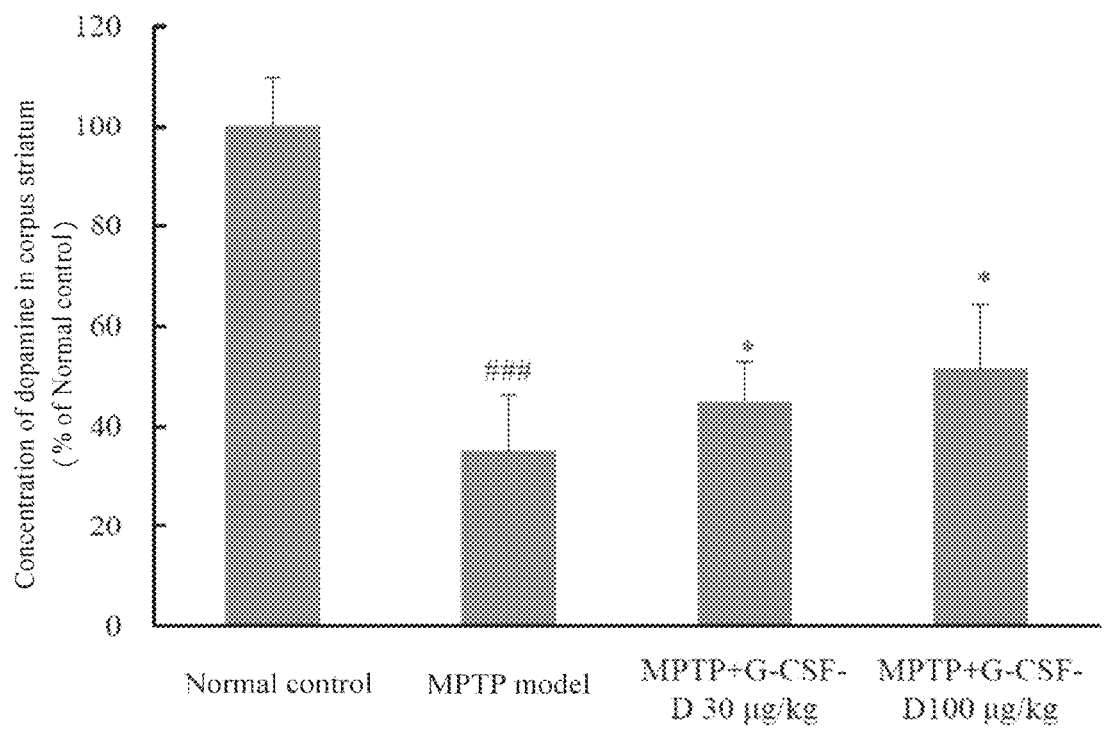
FIG. 4 is a graph showing the change in the concentration of dopamine in mouse corpus striatum.

Results as shown in FIG. 4 illustrate that the concentration of striatal dopamine decreased dramatically in the mice which were subjected to injection of MPTP for 5 consecutive days. G-CSF dimer treatment was able to increase the concentration of striatal dopamine in a dose-dependent manner.

The results show that MPTP caused a dramatic decline of the concentration of striatal dopamine as compared to normal control group (### p<0.001). G-CSF dimer was able to significantly prevent the decrease of concentration of striatal dopamine and increased the concentration of striatal dopamine in MPTP-induced mice. Moreover, G-CSF dimer treatment groups exhibited dose-dependent response and showed significant difference as compared to MPTP model group (*p<0.05).

b. Observation of Dopaminergic Nerve Fibers in Striatum and Dopaminergic Nerons in Substantia Nigra Methods: Mice were anesthetized with 10% chloral hydrate. After perfusion with 4% paraformaldehyde, brains were removed and fixed with 4% paraformaldehyde for 24 hours. The samples were transferred into 10%, 20%, 30% sucrose solutions gradient dehydration until sinking to the bottom. The midbrains and striatums were coronally sectioned into slices with thickness of 20 μm at −20° C. by freezing microtome, followed by TH immunohistochemical staining analysis. The slices of striatum and midbrain were incubated with the primary antibody which was a mouse monoclonal anti-TH antibody (1:1,000, Sigma) overnight at 4° C. After rinses in PBS for three times, the slices were incubated with biotin-conjugated secondary antibody (goat anti-mouse) at room temperature for 1 hr. SABC complexes were incubated at room temperature for 1 hr, followed by DAB staining, gradient dehydration in ethanol, transparency in xylene and the slides were sealed with neutral balsam. The optical density of TH-positive staining in striatums was scanned and the number of TH-positive cells in substantia nigra pars compacta was counted.

The results are shown in FIGS. 5A, 5B, 6A, and 6B.

Figure 5A:
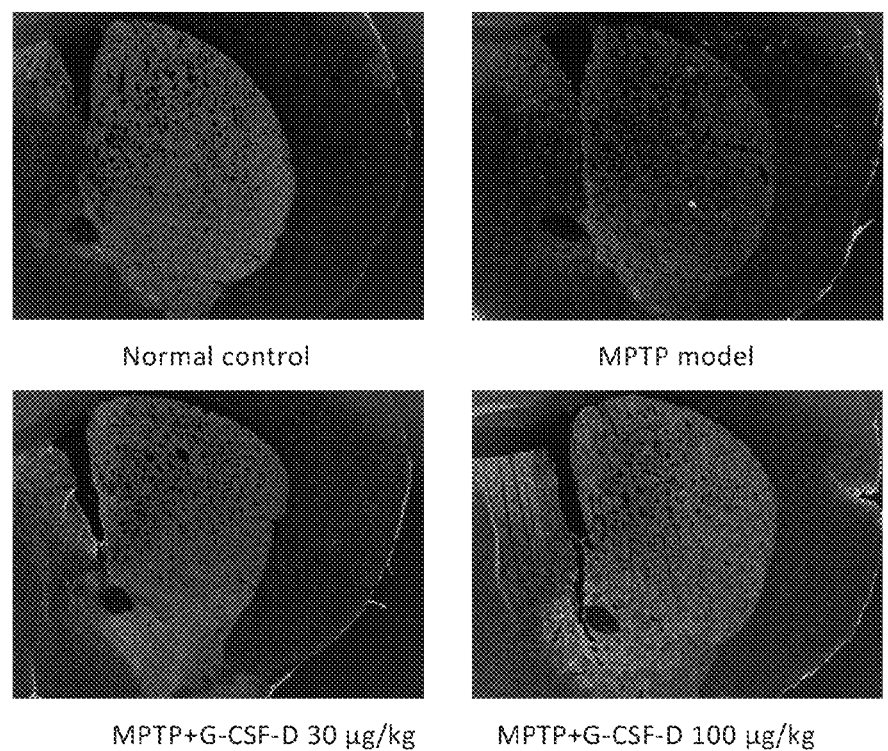
FIG. 5A is a series of representative graphs showing the immunohistochemical staining of TH-positive nerve fibers in mouse striatum.

FIG. 5A shows the immunohistochemical staining of TH-positive nerve fibers in mice striatums. The density of TH-positive nerve fibers in striatum decreased after the mice received 5 consecutive days injection of MPTP. G-CSF dimer treatment was shown to increase the number of TH-positive nerve fibers in a dose-dependent manner, indicating remarkable protective effect of G-CSF dimer from the loss of dopaminergic nerve fibers induced by MPTP.

Figure 5B:
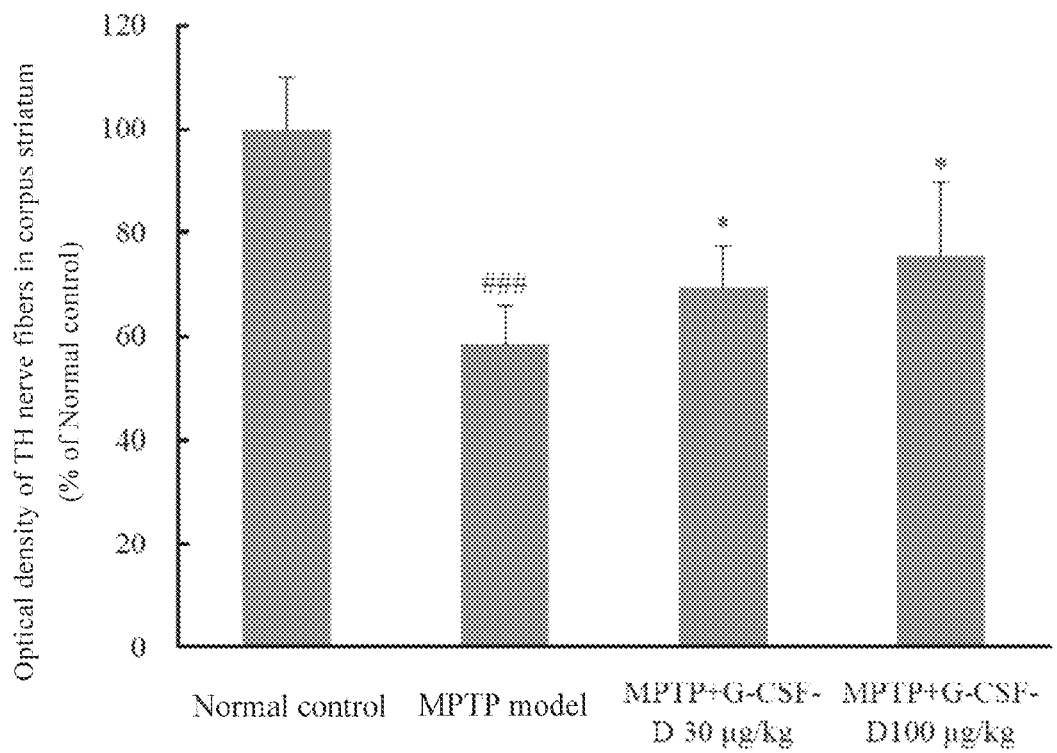
FIG. 5B shows the optical density of immunohistochemical staining of TH-positive nerver fibers in mouse striatum.

FIG. 5B shows the optical density of immunohistochemical staining for TH-positive nerve fibers in mice striatums. The results show that MPTP can induce substantial decrease of density of TH-positive nerve fibers in striatum (### $p<0.001$). Upon treatment with G-CSF dimer, the MPTP-induced reduction of the density of striatal TH-positive nerve fibers was significantly inhibited. G-CSF dimer treatment groups exhibited dose-dependent response and showed significant difference as compared to the MPTP model group (*$p<0.05$).

Figure 6A:
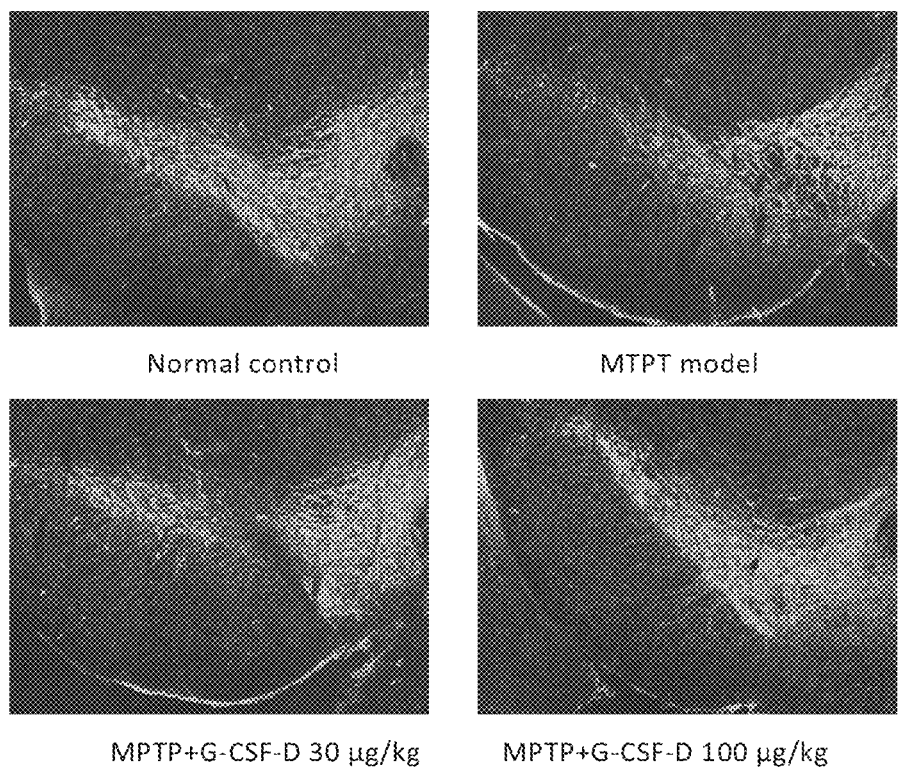
FIG. 6A is a series of representative graphs showing the immunohistochimical staining of TH-positive neurons in mouse substantia nigra pars compacta.

FIG. 6A shows the immunohistochemical staining of TH-positive neurons in substantia nigra par compacta in mice. The TH-positive neurons dropped greatly in substantia nigra pars compacta after the mice received 5 consecutive days injection of MPTP. G-CSF treatment restored the number of TH-positive neurons, indicating remarkable protective effect of G-CSF dimer from the massive loss of dopaminergic neurons induced with MPTP.

Figure 6B:
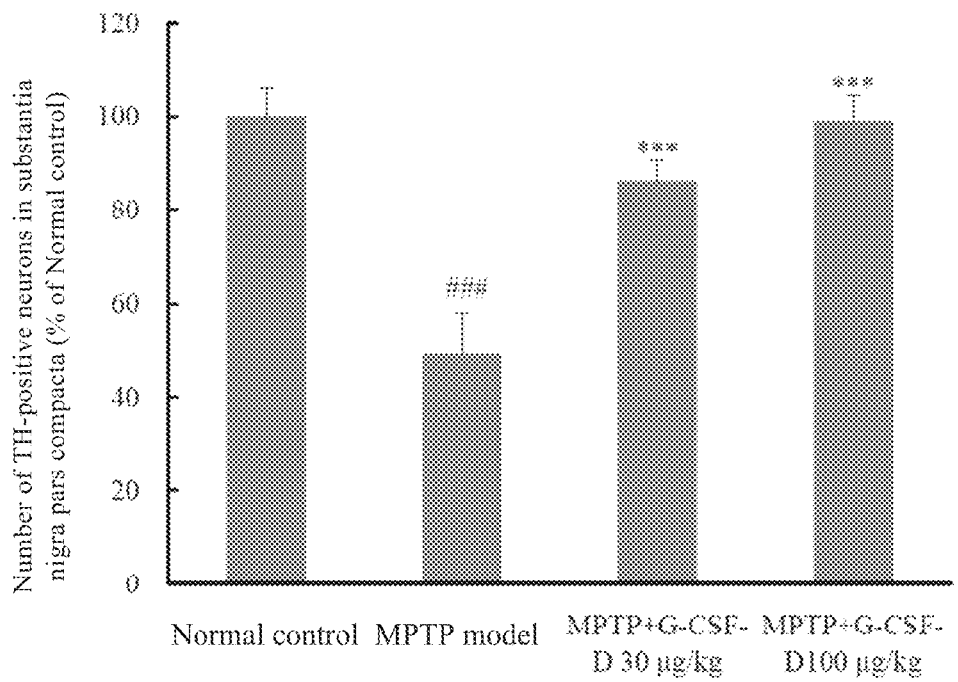
FIG. 6B shows the results of counting analysis of TH-positive cells in mouse substantia nigra pars compacta.

FIG. 6B shows the results of counting and analysis of TH-positive cells in substantia nigra pars compacta in mice. Compared to normal control group, the number of TH-positive neurons (about 49% of the normal control) was significantly reduced in substantia nigra par compacta after the mice received 5 consecutive days of injection of MPTP (###$p<0.001$), indicating that the massive loss of TH-positive dopaminergic neurons in substantia nigra resulted from MPTP induction. G-CSF dimer treatment significantly inhibited the loss of TH-positive neurons in substantia nigra pars compacta induced by MPTP and increased the number of TH-positive cells in substantia nigra in a dose-dependent manner. G-CSF dimer treatment groups exhibited dose-dependent response and showed significant difference as compared to the MPTP model group (***$p<0.001$). G-CSF treatment at 30 µg/kg or 100 µg/kg restored the number of TH-positive dopaminergic neurons in substantia nigra to about 86% and 99% of the normal control group, respectively. The TH-positive dopaminergic neurons of the G-CSF dimmer 100 µg/kg group amounted to that of the normal control group.

The results show that G-CSF dimer can significantly protect the dopaminergic neuron fibers from the loss induced by MPTP and can protect the dopaminergic neurons from the loss induced by MPTP.

Comparison example Therapeutic effect of G-CSF monomer on animals of PD model induced by MPTP.

Experimental methods (see US7723302): Mice received injection of MPTP at 30 mg/kg intraperitoneally once daily for 5 consecutive days, thus obtaining a PD mouse model. and the mice were allowed one day for recovery followed by 7 continuous days of daily administration of G-CSF (Neupogen, Amgen) at 250 µg/kg. After the last dose (after the end of administration), the numbers of TH-positive dopaminergic neurons in substantia nigra pars compacta were observed at different time points.

Model group: the number of TH-positive dopaminergic neurons in substantia nigra pars compacta before the first administration.

Normal group: the mice without injection of MPTP.

The number of TH-positive dopaminergic neurons in substantia nigra pars compacta was restored to about 70%, 80%, 77% of normal group on days 1, 7, and 14, respectively.

DISCUSSION

As shown in example 10, G-CSF dimer of the present invention was given intermittently at a dose of 30 µg/kg or 100 mg/kg for 3 times. On the first day after the last dose, the number of TH-positive neurons restored to about 86% and 99% in substantia nigra pars compacta in the 30 µg/kg and 100 µg/kg treatment groups, respectively. In particular, TH-positive neurons of the 100 µg/kg group was almost completely restored to the level of normal group on the first day after the last dose.

While in the comparison example, although G-CSF was administered at a dose of 250 µg/kg for 7 consecutive days, the TH-positive dopaminergic neuron was only restored to 70% of the normal group on the first day after the last dose.

The total dose of G-CSF dimer in the 100 µg/kg is 300 µg. The total dosage of G-CSF monomer in the comparison example is 1,750 µg.

According to the molar concentration of G-CSF monomer molecules, the molecular weight ratio of G-CSF monomer over G-CSF dimer is 1:5. Therefore, of the molar concentration of G-CSF monomer molecule in the G-CSF dimer 100 µg/kg group is only $\frac{1}{15}$ of that in the comparison example.

As indicated, the aforesaid G-CSF dimer of the present invention shows much lower dosage, better therapeutic effect as well as reduced administration frequency, thus it is greatly beneficial to the improvement of the compliance of patient treatment.

All references mentioned in the present invention are incorporated herein by reference as if each of those references has been incorporated by reference individually. Although the description referred to particular embodiments, it will be clear to a person skilled in the art that the present invention maybe practiced with variation of these specific details. Hence this invention should not be construed as limited to the embodiments set forth herein.

What is claimed is:

1. A method of treating Parkinson's disease in a subject in need of the treatment, the method comprising administering an effective amount of a granulocyte colony-stimulating factor ("G-CSF") dimer to a subject in need of the treatment, wherein the G-CSF dimer is a human G-CSF dimer, and wherein the human G-CSF dimer comprises two G-CSF-Fc complexes.

2. The method of claim 1, wherein said biological activity comprises:
   acting on neutrophil granulocytes and stem cells to drive the differentiation, growth, and maturation of neutrophils.

3. The method of claim 1, wherein the G-CSF dimer comprises Fc fragment of human IgG1, IgG2, IgG3, or IgG4.

4. The method of claim 1, wherein each said G-CSF-Fc complex comprises an amino acid sequence selected from the group consisting of SEQ ID NOs: 2-7.

5. The method of claim 1, wherein each said G-CSF-Fc complex comprises an amino acid sequence of SEQ ID NO: 6.

6. The method of claim 5, wherein each said G-CSF-Fc complex comprises an Fc fragment of human IgG2, and wherein said two Fc fragments in the G-CSF dimer are connected via a plurality of disulfide bonds disposed therebetween.

7. The method of claim 1, wherein the G-CSF dimer is present in a composition wherein 90-100% of the composition is the G-CSF dimer.

8. The method of claim 1, wherein said effective amount ranges from 0.01-300 mg of said G-CSF dimer per dose.

9. The method of claim 1, wherein said biological activity comprises activating mature neutrophils to participate in immune response.

10. The method of claim 1, wherein the subject is human.

11. The method of claim 1, wherein the G-CSF dimer is administered intravenously.

12. The method of claim 1, wherein the G-CSF dimer is administered subcutaneously.

13. The method of claim 1, wherein the G-CSF dimer is administered intra-arterially.

14. The method of claim 5, wherein said effective amount ranges from 0.01-300 mg of said G-CSF dimer per dose.

15. The method of claim 5, wherein the G-CSF dimer is administered intravenously.

16. The method of claim 6, wherein said effective amount ranges from 0.01-300 mg of said G-CSF dimer per dose.

17. The method of claim 6, wherein the G-CSF dimer is administered intravenously.

18. The method of claim 7, wherein said effective amount ranges from 0.01-300 mg of said G-CSF dimer per dose.

19. The method of claim 7, wherein the G-CSF dimer is administered intravenously.

20. The method of claim 8, wherein the G-CSF dimer is administered intravenously.

* * * * *